(12) United States Patent
Baba et al.

(10) Patent No.: US 7,037,954 B2
(45) Date of Patent: *May 2, 2006

(54) OCULAR LENS MATERIAL

(75) Inventors: Masaki Baba, Kasugai (JP); Tsuyoshi Watanabe, Kasugai (JP); Kazuhiko Nakada, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 31 days.

This patent is subject to a terminal disclaimer.

(21) Appl. No.: 10/648,489

(22) Filed: Aug. 27, 2003

(65) Prior Publication Data

US 2004/0039077 A1   Feb. 26, 2004

Related U.S. Application Data

(63) Continuation of application No. 09/926,560, filed as application No. PCT/JP01/02221 on Mar. 21, 2001, now Pat. No. 6,638,991.

(30) Foreign Application Priority Data

Mar. 22, 2000 (JP) .................. 2000-79862

(51) Int. Cl.
   *C08F 2/46* (2006.01)
   *C08F 2/50* (2006.01)

(52) U.S. Cl. ............... 522/99; 522/90; 522/91; 522/148; 522/172; 524/547; 524/279; 523/106; 523/107; 525/903; 525/906; 525/101

(58) Field of Classification Search ............. 522/99, 522/90, 91, 148, 172; 524/547, 279; 523/106, 523/107; 525/903, 906, 101

See application file for complete search history.

(56) References Cited

U.S. PATENT DOCUMENTS

| 5,346,946 A | 9/1994 | Yokoyama et al. |
| 5,556,929 A | 9/1996 | Yokoyama et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,849,811 A | 12/1998 | Nicolson et al. |
| 5,965,631 A | 10/1999 | Nicolson et al. |

FOREIGN PATENT DOCUMENTS

| EP | 584 826 A2 | 3/1994 |
| EP | 657 751 A2 | 6/1995 |
| EP | 0 769 723 A1 | 9/1997 |
| EP | 0 937 998 A2 | 8/1999 |
| JP | 3-228014 | 10/1991 |
| JP | 8-208761 | 8/1996 |

*Primary Examiner*—Sanza L. McClendon
(74) *Attorney, Agent, or Firm*—Armstrong, Kratz, Quintos, Hanson & Brooks, LLP

(57) ABSTRACT

An ocular lens material comprising a copolymer prepared by polymerization with heating of a monomer mixture and/or with irradiating a monomer mixture with ultraviolet ray by means of a molding method, the monomer mixture containing a polysiloxane macromonomer A, a Si-containing alkyl methacrylate B, a hydrophilic monomer C comprising NVP as C-1 and another hydrophilic monomer C-2, another monomer D and a crosslinkable monomer E comprising a crosslinkable monomer E-1 containing at least one group selected from acryloyl group, vinyl group and allyl group, and methacryloyl group, and a crosslinkable monomer E-2 containing at least two methacryloyl groups as main components, wherein (A+B)/C (weight ratio) is 30/70 to 70/30, A/B is 25/75 to 75/25, C-1/C-2 is 50/50 to 100/0, the amount of D is 0 to 20% by weight in the monomer mixture, which has high oxygen permeability, high mechanical strength, excellent surface wettability and low surface frictional property.

8 Claims, No Drawings

OCULAR LENS MATERIAL

This application is a continuation of prior application Ser. No. 09/926,560 filed Nov. 19, 2001 which is the National Stage of PCT/JP01/02221, filed Mar. 21, 2001.

TECHNICAL FIELD

The present invention relates to an ocular lens material. More particularly, the present invention relates to an ocular lens material having high oxygen permeability and excellent mechanical strength, and in addition, excellent surface wettability and low frictional surface property at the same time, which can be suitably used for a contact lens, an intraocular lens, an artificial cornea and the like.

BACKGROUND ART

Conventionally, a soft material has been a suitable material for a contact lens which can be worn comfortably and an intraocular lens which can be transformed and inserted only by small incision of the eyeball without damaging ocular tissue.

As the above soft material, there are a water-containing material which absorbs water, swells and softens, and a material which does not contain water substantially. Oxygen permeability of the water-containing material depends on water content and does not exceed larger than oxygen permeability of water.

Examples of materials from which a water-containing contact lens with high oxygen permeability can be produced is silicone-containing hydrogel, hereinafter referred to as silicone hydrogel, which is disclosed in Japanese Unexamined Patent Publication No. 179422/1991, Japanese Unexamined Patent Publication No. 196177/1991 and Japanese Unexamined Patent Publication No. 196118/1991. The silicone hydrogel is excellent in oxygen permeability because it has higher oxygen permeability than water.

The above silicone hydrogel contains a hydrophobic component, and therefore wettability of the material surface is inferior, resulting in high sticking property of the surface when the material is molded. Furthermore, when the amount of the silicon-containing monomer is increased to improve oxygen permeability of the material, the obtained material is semi-hard, and thus it is difficult to prepare from the material a contact lens which can be comfortably worn or an intraocular lens which can be inserted only by small incision. It is certain that subjective lens comfort becomes bad when such ocular lens is worn or put in. In addition, there is a defect that deposits such as lipid is increased because of high hydrophobic property. On the other hand, when a hydrophilic component is used in a large amount to improve feeling for wearing of the material, oxygen permeability of the material must depend on water content as a matter of course.

A hydrogel material most suitable for an ocular lens has high wettability and low frictional property in addition to high oxygen permeability and ideal rigidity. Such material is most appropriate because lubricity of a lens is maintained from high wettability and low frictional property, achieving comfortable wearing of the lens on the eye. To improve wettability and lower frictional property of a material, the following methods are suggested.

For instance, U.S. Pat. No. 4,099,859 specification discloses a method of covering surface of a contact lens with a hydrophilic monomer and irradiating the surface with ultraviolet ray to graft-polymerize the hydrophilic monomer on the surface of the contact lens material made of silicone rubber. In addition, U.S. Pat. No. 4,143,949 specification discloses a method of hydrophilic coating on a hydrophobic contact lens by radiation-induced polymerization, while each of U.S. Pat. No. 4,311,573 specification and U.S. Pat. No. 4,589,964 specification discloses a method of imparting hydrophilic property to surface of a hydrophobic polymer by graft-polymerizing a vinyl monomer according to decomposition of generated peroxyl group after ozone treatment. There is another disclosure in Japanese Patent Publication No. 2898664 that a crosslinked siloxane-urethane polymer in the state of an interpenetrating network polymer, generally referred to as IPN, with a hydrophilic vinyl polymer is obtained.

However, all of the above methods have various problems such that the method involves complicated steps, uniform treatment of all lenses and confirmation of the degree of treatment are difficult, and that preparation of raw materials is difficult. A desired hydrogel material most suitable for an ocular lens cannot be easily obtained according to these methods.

In addition to the above, the following various materials are proposed.

For instance, a water-insoluble hydrophilic gel comprising a crosslinked copolymer containing 20 to 90% by weight of water-soluble monomers and water-insoluble monomers such as methyl methacrylate and 10 to 80% by weight of a hydrophobic siloxane macromer is disclosed in Japanese Unexamined Patent Publication No. 22487/1979. A hydrophilic composition having improved flexibility and oxygen permeability after hydration, which is a copolymer of a comonomer comprising 15 to 65% by weight of an amide group-containing monomer, 10 to 75% by weight of an organic silicon compound and 0.1 to 65% by weight of an ester of an alkanol and a (meth)acrylic acid is disclosed in Japanese Unexamined Patent Publication No. 500418/1980. A polysiloxane contact lens obtained by polymerizing, with other monomers, a macromer prepared by mixing an organic siloxane oligomer (I) with a (meth)acrylate monomer (II) in a molar ratio (II)/(I) of 2.0 to 2.6 and reacting the mixture with diisocyanate is disclosed in Japanese Unexamined Patent Publication No. 46311/1992. An ocular lens material comprising a copolymer containing a polysiloxane macromonomer and an alkyl(meth)acrylamide as main components in a weight ratio, the polysiloxane macromonomer/the alkyl(meth)acrylamide, of 5/95 to 90/10 is disclosed in Japanese Unexamined Patent Publication No. 121826/1994.

Being obtained from a component containing silicon, particularly silicone, all of the above gel, composition, contact lens and material have excellent oxygen permeability. However, surface wettability is not particularly good or friction property is not sufficiently low, which means that oxygen permeability, surface wettability and low friction property are not achieved simultaneously.

The present invention has been carried in view of the above prior arts. The object of the present invention is to provide an ocular lens material having excellent surface wettability and low surface frictional property in addition to high oxygen permeability and high mechanical strength.

DISCLOSURE OF INVENTION

The present invention relates to an ocular lens material comprising a copolymer prepared by polymerization with heating a monomer mixture and/or with irradiating a monomer mixture with ultraviolet ray by means of a molding method, said monomer mixture containing, as main components, (A) a polysiloxane macromonomer in which a polymerizable group bonds to a siloxane main chain through at least one urethane bond, and which is represented by the formula (I):

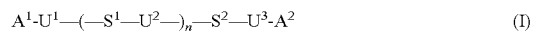

wherein $A^1$ is a group represented by the formula (II):

$$Y^{21}\text{-}Z^{21}\text{-}R^{31}\text{—} \quad (II)$$

in which $Y^{21}$ is acryloyl group, vinyl group or allyl group, $Z^{21}$ is oxygen atom or direct bond, and $R^{31}$ is direct bond or a linear, branched or aromatic alkylene group having 1 to 12 carbon atoms;

$A^2$ is a group represented by the formula (III):

$$\text{—}R^{34}\text{-}Z^{22}\text{-}Y^{22} \quad (III)$$

in which $Y^{22}$ is acryloyl group, vinyl group or allyl group, $Z^{22}$ is oxygen atom or direct bond, and $R^{34}$ is direct bond or a linear, branched or aromatic alkylene group having 1 to 12 carbon atoms, where $Y^{21}$ in the formula (II) and $Y^{22}$ in the formula (III) may be the same or different;

$U^1$ is a group represented by the formula (IV):

$$\text{—}X^{21}\text{-}E^{21}\text{-}X^{25}\text{—}R^{32}\text{—} \quad (IV)$$

in which each of $X^{21}$ and $X^{25}$ is independently selected from direct bond, oxygen atom and an alkylene glycol group, $E^{21}$ is —NHCO— group (in this case, $X^{21}$ is direct bond, $X^{25}$ is oxygen atom or an alkylene glycol group and $E^{21}$ and $X^{25}$ form urethane bond), —CONH— group (in this case, $X^{21}$ is oxygen atom or an alkylene glycol group, $X^{25}$ is direct bond and $E^{21}$ and $X^{21}$ form urethane bond) or a divalent group derived from a diisocyanate selected from a group of a saturated or unsaturated aliphatic diisocyanate, an alicyclic diisocyanate and an aromatic diisocyanate (in this case, each of $X^{21}$ and $X^{25}$ is independently selected from oxygen atom and an alkylene glycol group and $E^{21}$ and $X^{21}$, $E^{21}$ and $X^{25}$ form two urethane bonds, respectively) and $R^{32}$ is a linear or branched alkylene group having 1 to 6 carbon atoms;

each of $S^1$ and $S^2$ is independently a group represented by the formula (V):

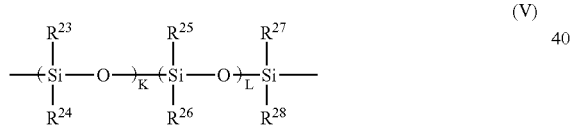

in which each of $R^{23}$, $R^{24}$, $R^{25}$, $R^{26}$, $R^{27}$ and $R^{28}$ is independently an alkyl group having 1 to 6 carbon atoms, an alkyl group substituted with fluorine atom or phenyl group, K is an integer of 1 to 1,500, L is 0 or an integer of 1 to 1,499, and K+L is an integer of 1 to 1,500;

$U^2$ is a group represented by the formula (VI):

$$\text{—}R^{37}\text{—}X^{27}\text{-}E^{24}\text{-}X^{28}\text{—}R^{38}\text{—} \quad (VI)$$

in which each of $R^{37}$ and $R^{38}$ is independently a linear or branched alkylene group having 1 to 6 carbon atoms, each of $X^{27}$ and $X^{28}$ is independently oxygen atom or an alkylene glycol group, and $E^{24}$ is a divalent group derived from a diisocyanate selected from a group of a saturated or unsaturated aliphatic diisocyanate, an alicyclic diisocyanate and an aromatic diisocyanate (in this case, $E^{24}$ and $X^{27}$, $E^{24}$ and $X^{28}$ form two urethane bonds, respectively);

$U^3$ is a group represented by the formula (VII):

$$\text{—}R^{33}\text{—}X^{26}\text{-}E^{22}\text{-}X^{22}\text{—} \quad (VII)$$

in which $R^{33}$ is a linear or branched alkylene group having 1 to 6 carbon atoms, each of $X^{22}$ and $X^{26}$ is independently selected from direct bond, oxygen atom and an alkylene glycol group, $E^{22}$ is —NHCO— group (in this case, $X^{22}$ is oxygen atom or an alkylene glycol group, $X^{26}$ is direct bond and $E^{22}$ and $X^{22}$ form urethane bond), —CONH— group (in this case, $X^{22}$ is direct bond, $X^{26}$ is oxygen atom or an alkylene glycol group and $E^{22}$ and $X^{26}$ form urethane bond) or a divalent group derived from a diisocyanate selected from a group of a saturated or unsaturated aliphatic diisocyanate, an alicyclic diisocyanate and an aromatic diisocyanate (in this case, each of $X^{22}$ and $X^{26}$ is independently oxygen atom or an alkylene glycol group and $E^{22}$ and $X^{22}$, $E^{22}$ and $X^{26}$ form two urethane bonds, respectively); and n is 0 or an integer of 1 to 10, (B) a silicon-containing alkyl methacrylate,
(C) a hydrophilic monomer comprising
(C-1) N-vinylpyrrolidone and
(C-2) a hydrophilic monomer excepting N-vinylpyrrolidone (C-1), containing acryloyl group, vinyl group or allyl group;
(D) at least one monomer selected from an alkyl(meth)acrylate and a fluorine-containing alkyl(meth)acrylate; and
(E) a low molecular weight crosslinkable monomer comprising
(E-1) a crosslinkable monomer containing at least one group selected from acryloyl group, vinyl group and allyl group, and another group of methacryloyl group, and
(E-2) a crosslinkable monomer containing at least two methacryloyl groups,
wherein the weight ratio of the total of the polysiloxane macromonomer (A) and the silicon-containing alkyl methacrylate (B) to the hydrophilic monomer (C), the total weight of (A) and (B)/the weight of (C), is 30/70 to 70/30,
the weight ratio of the polysiloxane macromonomer (A) to the silicon-containing alkyl methacrylate (B), the weight of (A)/the weight of (B), is 25/75 to 75/25,
the weight ratio of N-vinylpyrrolidone (C-1) to the hydrophilic monomer (C-2), the weight of (C-1)/the weight of (C-2), is 50/50 to 100/0, and the amount of the monomer (D) in the monomer mixture is 0 to 20% by weight.

BEST MODE FOR CARRYING OUT THE INVENTION

The ocular lens material of the present invention comprises a copolymer prepared by polymerization with heating a monomer mixture and/or with irradiating a monomer mixture with ultraviolet ray by means of a molding method, the monomer mixture containing, as main components, a polysiloxane macromonomer (A) represented by the formula (I), $$A^1\text{-}U^1\text{—}(\text{—}S^1\text{—}U^2\text{—})_n\text{—}S^2\text{—}U^3\text{-}A^2 \quad (I)$$

wherein each of $A^1$, $A^2$, $U^1$, $U^2$, $U^3$, $S^1$, $S^2$ and n is the same as the above; a silicon-containing alkyl methacrylate (B); a hydrophilic monomer (C) comprising N-vinylpyrrolidone (C-1) and a hydrophilic monomer (C-2) excepting N-vinylpyrrolidone (C-1), containing acryloyl group, vinyl group or allyl group; at least one monomer (D) selected from an alkyl(meth)acrylate and a fluorine-containing alkyl(meth)acrylate; and a crosslinkable monomer (E) comprising a crosslinkable monomer (E-1) containing at least one group selected from acryloyl group, vinyl group and allyl group, and another group of methacryloyl group, and a crosslinkable monomer (E-2) containing at least two methacryloyl groups.

High oxygen permeability is imparted since the polysiloxane macromonomer (A) contains silicone chains in its molecular chain. In addition, the polysiloxane macromonomer (A) has elastic urethane bonds, and which can improve mechanical strength without spoiling flexibility and oxygen permeability of polysiloxane, removing brittleness by imparting elastic recovery and improving mechanical strength.

The polysiloxane macromonomer (A) has a polymerizable group at each terminal of the molecule, through which copolymerization with other copolymerization components occurs, and thus has excellent characteristics of imparting to the obtained ocular lens material not only physical reinforcing effect by intertwisting of molecule but also reinforcing effect from chemical bond, i.e., covalent bond. In other words, the polysiloxane macromonomer (A) acts as a high molecular weight crosslinkable monomer.

The polysiloxane macromonomer (A) is a compound represented by the formula (I).

In the formula (I) as mentioned above, $A^1$ is a group represented by the formula (II):

$$Y^{21}\text{-}Z^{21}\text{-}R^{31}\text{—} \tag{II}$$

wherein each of $Y^{21}$, $Z^{21}$ and $R^{31}$ is the same as the above, and $A^2$ is a group represented by the formula (III):

$$\text{—}R^{34}\text{-}Z^{22}\text{-}Y^{22} \tag{III}$$

wherein each of $Y^{22}$, $Z^{22}$ and $R^{34}$ is the same as the above.

Both $Y^{21}$ and $Y^{22}$ are a polymerizable group and preferably acryloyl group from the viewpoint that they can copolymerize with the hydrophilic monomer (C) easily.

Both $Z^{21}$ and $Z^{22}$ are oxygen atom or direct bond, preferably oxygen atom.

Both $R^{31}$ and $R^{34}$ are direct bond or a linear, branched or aromatic alkylene group having 1 to 12 carbon atoms, preferably ethylene group, propylene group or butylene group.

All of $U^1$, $U^2$ and $U^3$ are a group having urethane bond in the molecular chain of the polysiloxane macromonomer (A).

In $U^1$ and $U^3$, each of $E^{21}$ and $E^{22}$ is —CONH— group, —NHCO— group or a divalent group derived from a diisocyanate selected from a group of a saturated or unsaturated aliphatic diisocyanate, an alicyclic diisocyanate and an aromatic diisocyanate as mentioned above. Herein, examples of the divalent group derived from a diisocyanate selected from a group of a saturated or unsaturated aliphatic diisocyanate, an alicyclic diisocyanate and an aromatic diisocyanate are, for instance, a divalent group derived from a saturated aliphatic diisocyanate such as ethylenediisocyanate, 1,3-diisocyanatepropane or hexamethylenediisocyanate; a divalent group derived from an alicyclic diisocyanate such as 1,2-diisocyanatecyclohexane, bis(4-isocyanatecyclohexyl)methane or isophoronediisocyanate; a divalent group derived from an aromatic diisocyanate such as tolylenediisocyanate or 1,5-diisocyanatenaphthalene; and a divalent group derived from an unsaturated aliphatic diisocyanate such as 2,2'-diisocyanatediethylfumarate. Among these, a divalent group derived from hexamethylenediisocyanate, a divalent group derived from tolylenediisocyanate and a divalent group derived from isophoronediisocyanate are preferable since they are relatively easy to be obtained and can easily impart mechanical strength.

Referring to $U^1$, when $E^{21}$ is —NHCO— group, $X^{21}$ is direct bond, $X^{25}$ is oxygen atom or an alkylene glycol group, and $E^{21}$ and $X^{25}$ form urethane bond represented by the formula —NHCOO—. When $E^{21}$ is —CONH— group, $X^{21}$ is oxygen atom or an alkylene glycol group, $X^{25}$ is direct bond, and $E^{21}$ and $X^{21}$ form urethane bond represented by the formula —OCONH—. When $E^{21}$ is a divalent group derived from a diisocyanate mentioned above, each of $X^{21}$ and $X^{25}$ is independently selected from oxygen atom and preferably an alkylene glycol group having 1 to 6 carbon atoms, $E^{21}$ and $X^{21}$, $E^{21}$ and $X^{25}$ form two urethane bonds, respectively. $R^{32}$ is a linear or branched alkylene group having 1 to 6 carbon atoms.

Referring to $U^2$, $E^{24}$ is a divalent group derived from a diisocyanate selected from a group of a saturated or unsaturated aliphatic diisocyanate, an alicyclic diisocyanate and an aromatic diisocyanate as mentioned above. Herein, examples of the divalent group derived from a diisocyanate selected from a group of a saturated or unsaturated aliphatic diisocyanate, an alicyclic diisocyanate and an aromatic diisocyanate are the same as those in the above $U^1$ and $U^3$. Among them, however, a divalent group derived from hexamethylenediisocyanate, a divalent group derived from tolylenediisocyanate and a divalent group derived from isophoronediisocyanate are preferable since they are relatively easy to be obtained and can easily impart mechanical strength. Also, $E^{24}$ and $X^{27}$, $E^{24}$ and $X^{28}$ form two urethane bonds, respectively. Each of $X^{27}$ and $X^{28}$ is independently oxygen atom or preferably an alkylene glycol group having 1 to 6 carbon atoms. Each of $R^{37}$ and $R^{38}$ is independently a linear or branched alkylene group having 1 to 6 carbon atoms.

Referring to $U^3$, $R^{33}$ is a linear or branched alkylene group having 1 to 6 carbon atoms. When $E^{22}$ is —NHCO— group, $X^{22}$ is oxygen atom or an alkylene glycol group, $X^{26}$ is direct bond, and $E^{22}$ and $X^{22}$ form urethane bond represented by the formula —NHCOO—. When $E^{22}$ is —CONH— group, $X^{22}$ is direct bond, $X^{26}$ is oxygen atom or an alkylene glycol group, and $E^{22}$ and $X^{26}$ form urethane bond represented by the formula —OCONH—. When $E^{22}$ is a divalent group derived from a diisocyanate mentioned above, each of $X^{22}$ and $X^{26}$ is independently selected from oxygen atom and preferably an alkylene glycol group having 1 to 6 carbon atoms, and $E^{22}$ and $X^{22}$, $E^{22}$ and $X^{26}$ form two urethane bonds, respectively.

Herein, examples of the preferable alkylene glycol having 1 to 6 carbon atoms in the above $X^{21}$, $X^{25}$, $X^{27}$, $X^{28}$, $X^{22}$ and $X^{26}$ are a group represented by the formula (VIII):

$$\text{—O—}(C_xH_{2x}\text{—O})_y\text{—} \tag{VIII}$$

wherein x is an integer of 1 to 4 and y is an integer of 1 to 5. When y is an integer of at least 6 in the formula (VIII), oxygen permeability and mechanical strength tend to be lowered. Therefore, in the present invention, y is preferably an integer of 1 to 5, more preferably an integer of 1 to 3.

Each of $S^1$ and $S^2$ is a group represented by the formula (V) as mentioned above.

In the formula (V), each of $R^{23}$, $R^{24}$, $R^{25}$, $R^{26}$, $R^{27}$ and $R^{28}$ is independently an alkyl group having 1 to 6 carbon atoms, an alkyl group substituted with fluorine atom or phenyl group as mentioned above.

Concrete examples of the alkyl group substituted with fluorine atom are 3,3,3-trifluoro-n-propyl group, 3,3,3-trifluoroisopropyl group, 3,3,3-trifluoro-n-butyl group, 3,3,3-trifluoroisobutyl group, 3,3,3-trifluoro-sec-butyl group, 3,3,3-trifluoro-t-butyl group, 3,3,3-trifluoro-n-pentyl group, 3,3,3-trifluoroisopentyl group, 3,3,3-trifluorothiopentyl group, 3,3,3-trifluorohexyl group and the like. When a polysiloxane macromonomer (A) having the above alkyl group substituted with fluorine atom is used in an increased amount, there is a tendency that lipid-stain resistance of the ocular lens material to be obtained is further improved.

K is an integer of 1 to 1,500, L is 0 or an integer of 1 to 1,499 and K+L is an integer of 1 to 1,500. When K+L is larger than 1,500, molecular weight of the polysiloxane macromonomer (A) is large and solubility thereof with the hydrophilic monomer (C) is inferior. Accordingly, there is a tendency that the mixture at mixing does not dissolve sufficiently or becomes opaque at polymerization, resulting in the fact that a homogeneous and transparent ocular lens material cannot be obtained. Also, when K+L is 0, there is a tendency that not only oxygen permeability but also flexibility of an ocular lens material is lowered. K+L is an integer of preferably 2 to 1,000, more preferably 3 to 500.

In addition, n is 0 or an integer of 1 to 10. When n is larger than 10, molecular weight of the polysiloxane macromonomer (A) is large and solubility thereof with the hydrophilic monomer (C) is inferior. Accordingly, there is a tendency that the mixture at mixing does not dissolve sufficiently or becomes opaque at polymerization, resulting in the fact that a homogeneous and transparent ocular lens material cannot be obtained. Preferably, n is 0 or an integer of 1 to 5.

Typical examples of the polysiloxane macromonomer (A) are a macromonomer, hereinafter referred to as macromonomer (A-1), represented by the formula:

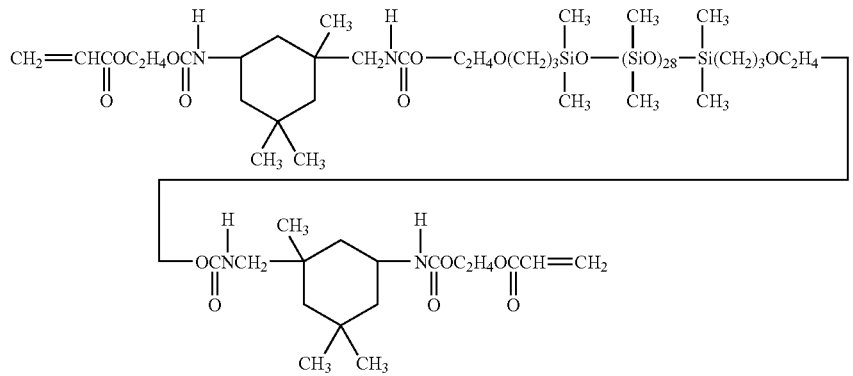

a macromonomer, hereinafter referred to as macromonomer (A-2), represented by the formula:

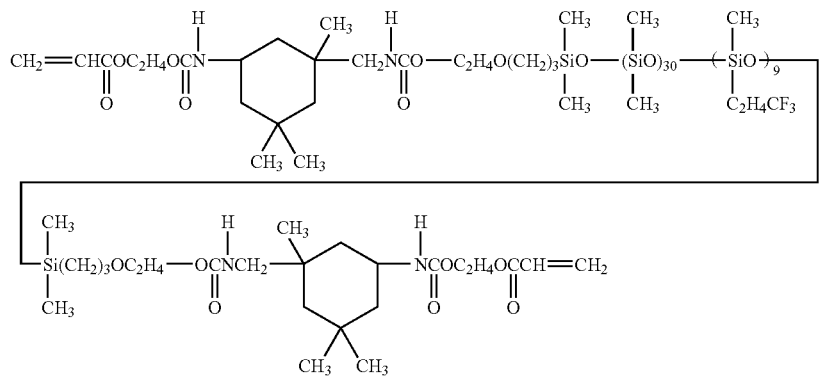

and the like. These can be used alone or in admixture thereof.

The above silicon-containing alkyl methacrylate (B) is a component which imparts further improved oxygen permeability to an ocular lens material.

One of the major characteristics of the present invention is that the polymerizable group in the silicon-containing alkyl methacrylate (B) is methacryloyl group while the polymerizable groups in the polysiloxane macromonomer (A), namely, both $Y^{21}$ in the formula (II) representing $A^1$ in the formula (I) and $Y^{22}$ in the formula (III) representing $A^2$ in the formula (I) are a group selected from acryloyl group, vinyl group and allyl group. Since the polysiloxane macromonomer (A) and the silicon-containing alkyl methacrylate (B) have a different polymerizable group in this way, a silicone block segment is introduced to the main chain, enabling a hydrophilic segment derived from the hydrophilic monomer (C) mentioned below to form a block and be introduced into the silicone segment. Besides, since both of the polysiloxane macromonomer (A) and the hydrophilic monomer (C) have a polymerizable group selected from acryloyl group, vinyl group and allyl group, copolymerization proceeds effectively. On the other hand, when the polysiloxane macromonomer (A) and the silicon-containing alkyl methacrylate (B) have the same polymerizable group, there is a problem that a particularly large domain is formed since both components contain silicon.

Typical examples of the silicon-containing alkyl methacrylate (B) are trimethylsiloxydimethylsilylmethyl methacrylate, trimethylsiloxydimethylsilylpropyl methacrylate, methylbis(trimethylsiloxy)silylpropyl methacrylate, tris(trimethylsiloxy)silylpropyl methacrylate, mono[methylbis(trimethylsiloxy)siloxy]bis(trimethylsiloxy)silylpropyl methacrylate, tris[methylbis(trimethylsiloxy)siloxy]silylpropyl methacrylate, methylbis(trimethylsiloxy)silylpropylglyceryl methacrylate, tris(trimethylsiloxy)silylpropylglyceryl methacrylate, mono[methylbis(trimethylsiloxy)siloxy]bis(trimethylsiloxy)silylpropylglyceryl methacrylate, trimethylsilylethyltetramethyldisiloxypropylglyceryl methacrylate, trimethylsilylmethyl methacrylate, trimethylsilylpropyl methacrylate, trimethylsilylpropylglyceryl methacrylate, trimethylsiloxydimethylsilylpropylglyceryl methacrylate, methylbis(trimethylsiloxy)silylethyltetramethyldisiloxymethyl methacrylate, tetramethyltriisopropylcyclotetrasiloxanylpropyl methacrylate, tetramethyltriisopropylcyclotetrasiloxybis(trimethylsiloxy)silylpropyl methacrylate and the like. These can be used alone or in admixture thereof.

The above hydrophilic monomer (C) is a component which imparts flexibility and surface wettability to the ocular lens material to be obtained, improving feeling for wearing and achieving low frictional property.

Another major characteristic of the present invention is that N-vinylpyrrolidone (C-1) and a hydrophilic monomer (C-2) excepting N-vinylpyrrolidone (C-1), containing acryloyl group, vinyl group or allyl group are used together as the above hydrophilic monomer (C). That is, although compatibility with silicon-containing components, i.e., the polysiloxane macromonomer (A) and the silicon-containing alkyl methacrylate (B), is inferior and transparency of the ocular lens material to be obtained is lowered when only N-vinylpyrrolidone (C-1) is used, such compatibility with the silicon-containing components is improved by the simultaneous use of the above hydrophilic monomer (C-2). On the other hand, when N-vinylpyrrolidone (C-1) is not used, desirable low frictional property, lubricity and stain resistance cannot be imparted to the ocular lens material. From these facts, it is essential to use N-vinylpyrrolidone (C-1) and the hydrophilic monomer (C-2) together, and the polymerizable group in the hydrophilic monomer (C-2) is acryloyl group, vinyl group or allyl group in consideration of copolymerizability with N-vinylpyrrolidone (C-1).

Typical examples of the hydrophilic monomer (C-2) are an acrylamide monomer such as acrylamide, N,N-dimethylacrylamide, N,N-diethylacrylamide, N,N-dimethylaminopropylacrylamide, N-isopropylacrylamide, or acryloylmorpholine; a hydroxyalkyl acrylate such as 2-hydroxyethyl acrylate, hydroxypropyl acrylate or hydroxybutyl acrylate; an (alkyl)aminoalkyl acrylate such as 2-dimethylaminoethyl acrylate or 2-butylaminoethyl acrylate; alkylene glycol monoacrylate such as ethylene glycol monoacrylate or propylene glycol monoacrylate; a poly(alkylene glycol) monoacrylate such as polyethylene glycol monoacrylate or polypropylene glycol monoacrylate; ethylene glycol allyl ether; ethylene glycol vinyl ether; acrylic acid; an aminostyrene; a hydroxystyrene; vinyl acetate; glycidyl acrylate; allyl glycidyl ether; vinyl propionate; an N-vinyl lactam such as N-vinyl-3-methyl-2-pyrrolidone, N-vinyl-4-methyl-2-pyrrolidone, N-vinyl-5-methyl-2-pyrrolidone, N-vinyl-6-methyl-2-pyrrolidone, N-vinyl-3-ethyl-2-pyrrolidone, N-vinyl-4,5-dimethyl-2-pyrrolidone, N-vinyl-5,5-dimethyl-2-pyrrolidone, N-vinyl-3,3,5-trimethyl-2-pyrrolidone, N-vinyl-2-piperidone, N-vinyl-3-methyl-2-piperidone, N-vinyl-4-methyl-2-piperidone, N-vinyl-5-methyl-2-piperidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-2-caprolactam, N-vinyl-3-methyl-2-caprolactam, N-vinyl-4-methyl-2-caprolactam, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam; an N-vinylamide such as N-vinylformamide, N-vinyl-N-methylformamide, N-vinyl-N-ethylformamide, N-vinylacetoamide, N-vinyl-N-methylacetoamide, N-vinyl-N-ethylacetoamide or N-vinylphthalimide; and the like. These can be used alone or in admixture thereof.

Among the above hydrophilic monomer (C-2), at least one selected from acrylamide, N,N-dimethylacrylamide, N,N-diethylacrylamide, N-isopropylacrylamide, acryloylmorpholine, 2-hydroxyethylacrylate, 2-dimethylaminoethyl acrylate and vinyl acetate is preferable from the viewpoint of supirior compatibility with a silicon-containing component. In particular, N,N-dimethylacrylamide is preferable.

When a component such as vinyl acetate which is hydrolyzable with acid or base is used in the polymerization system to prepare an ocular lens material, treatment with acid or base can impart further flexibility and surface wettability to the ocular lens.

The ratio of N-vinylpyrrolidone (C-1) to the hydrophilic monomer (C-2), the weight of (C-1)/the weight of (C-2), is at least 50/50, preferably at least 55/45 and more preferably at least 60/40. This is because surface wettability and low frictional property of an ocular lens material may be lowered when the amount of N-vinylpyrrolidone (C-1) is small. On the other hand, the ratio is at most 100/0, preferably at most 95/5 and more preferably at most 90/10 because not only the polymer mixture becomes opaque to lower transparency of the ocular lens material, but also hardness of the material itself is increased, which may have harmful effect on feeling for wearing when the amount of N-vinylpyrrolidone (C-1) is large.

The respective ratios concerning the polysiloxane macromonomer (A), the silicon-containing alkylmethacrylate (B) and the hydrophilic monomer (C) which are essential components for preparing an ocular lens material of the present invention are defined as follow.

The ratio of the total of the polysiloxane macromonomer (A) and the silicon-containing alkylmethacrylate (B) to the hydrophilic monomer (C), the total weight of (A) and (B)/the weight of (C), is at least 30/70, preferably at least 35/65 and more preferably at least 40/60. This is because oxygen permeability of ocular lens material is likely to depend on water content, making it impossible to achieve high oxygen permeability when the amount of the hydrophilic monomer (C) is large. On the other hand, the ratio is at most 70/30, preferably at most 67/33 and more preferably at most 65/35 because the ocular lens material becomes less flexible, and hard, or sticky on the surface, which may have harmful effect on feeling for wearing when the total amount of the polysiloxane macromonomer (A) and the silicon-containing alkylmethacrylate (B) is large.

There is another condition required concurrently with the above ratio of the total of the polysiloxane macromonomer (A) and the silicon-containing alkylmethacrylate (B) to the hydrophilic monomer (C), the total weight of (A) and (B)/the weight of (C). That is the ratio of the polysiloxane macromonomer (A) to the silicon-containing alkylmethacrylate (B), the weight of (A)/the weight of (B), which is at least 25/75, preferably at least 30/70 and more preferably at least 35/65. This is because the surface of the ocular lens material becomes extremely sticky and shape stability of the material is lowered when the amount of the silicon-containing alkylmethacrylate (B) is large. On the other hand, the ratio is at most 75/25, preferably at most 73/27 and more preferably at most 70/30 because the ocular lens material becomes less flexible but hard and brittle when the amount of the polysiloxane macromonomer (A) is large.

The monomer (D) is used when it is desired to impart another property to an ocular lens material.

The above monomer (D) is at least one selected from an alkyl(meth)acrylate and a fluorine-containing alkyl(meth)acrylate.

The alkyl(meth)acrylate is a component which impart hardness or softness to an ocular lens material by adjusting degree of hardness of the ocular lens material.

Typical examples of an alkyl(meth)acrylate are a linear, branched or cyclic alkyl(meth)acrylate such as methyl (meth)acrylate, ethyl(meth)acrylate, isopropyl(meth)acrylate, n-propyl(meth)acrylate, isobutyl(meth)acrylate, n-butyl(meth)acrylate, 2-ethylhexyl(meth)acrylate, n-octyl (meth)acrylate, n-decyl(meth)acrylate, n-dodecyl(meth) acrylate, t-butyl(meth)acrylate, pentyl(meth)acrylate, t-pentyl (meth)acrylate, hexyl(meth)acrylate, heptyl(meth) acrylate, nonyl (meth)acrlate, stearyl(meth)acrylate, cyclopentyl(meth)acrylate, cyclohexyl(meth)acrylate and the like. These can be used alone or in admixture thereof.

In the instant specification, "-(meth)acrylate" means "-acrylate and/or -methacrylate". The same definition applies to other (meth)acrylate derivatives.

The fluorine-containing alkyl(meth)acrylate is a component which improves lipid-stain resistance of an ocular lens material.

Examples of the fluorine-containing alkyl(meth)acrylate are, for instance, a compound represented by the formula (X):

$$CH_2=CR^4COOC_sH_{(2s-t+1)}F_t \quad (X)$$

wherein $R^4$ is hydrogen atom or $CH_3$, s is an integer of 1 to 15 and t is an integer of 1 to (2s+1), and the like.

Typical examples of the compound represented by the above formula (X) are 2,2,2-trifluoroethyl(meth)acrylate, 2,2,3,3-tetrafluoropropyl(meth)acrylate, 2,2,3,3-tetrafluoro-t-pentyl(meth)acrylate, 2,2,3,4,4,4-hexafluorobutyl(meth) acrylate, 2,2,3,4,4,4-hexafluoro-t-hexyl(meth)acrylate, 2,3,4,5,5,5-hexafluoro-2,4-bis(trifluoromethyl)pentyl(meth) acrylate, 2,2,3,3,4,4-hexafluorobutyl(meth)acrylate, 2,2,2,2', 2',2'-hexafluoroisopropyl(meth)acrylate, 2,2,3,3,4,4,4-heptafluorobutyl(meth)acrylate, 2,2,3,3,4,4,5,5-octafluoropentyl(meth)acrylate, 2,2,3,3,4,4,5,5,5-nonafluoropentyl(meth)acrylate, 2,2,3,3,4,4,5,5,6,6,7,7-dodecafluoroheptyl(meth)acrylate, 3,3,4,4,5,5,6,6,7,7,8,8-dodecafluorooctyl(meth)acrylate, 3,3,4,4,5,5,6,6,7,7,8,8,8-tridecafluorooctyl(meth)acrylate, 2,2,3,3,4,4,5,5,6,6,7,7,7-tridecafluoroheptyl(meth)acrylate, 3,3,4,4,5,5,6,6,7,7,8,8,9,9,10,10-hexadecafluorodecyl(meth)acrylate, 3,3,4,4,5,5,6,6,7,7,8,8,9,9,10,10,10-heptadecafluorodecyl(meth)acrylate, 3,3,4,4,5,5,6,6,7,7,8,8,9,9,10,10,11,11-octadecafluoroundecyl(meth)acrylate, 3,3,4,4,5,5,6,6,7,7,8,8,9,9,10,10,11,11,11-nonadecafluoroundecyl(meth)acrylate, 3,3,4,4,5,5,6,6,7,7,8,8,9,9,10,10,11,11,12,12-eicosafluorododecyl(meth) acrylate and the like. These can be used alone or in admixture thereof.

The amount of monomer (D) is at most 20% by weight, preferably at most 10% by weight in order to achieve sufficient effect from the polysiloxane macromonomer (A), the silicon-containing alkyl methacrylate (B) and the hydrophilic monomer (C). When the monomer (D) is used, the amount is at least 0.01% by weight, preferably at least 0.1% by weight in order to achieve sufficient effect therefrom.

The crosslinkable monomer (E) is a component which improves mechanical strength of the ocular lens material to impart durability thereto.

Another major characteristic of the present invention is that a crosslinkable monomer (E-1) containing at least one group selected from acryloyl group, vinyl group and allyl group, and another group of methacryloyl group, and a crosslinkable monomer (E-2) containing at least two methacryloyl groups are used together as the crosslinkable monomer (E).

Typical examples of the crosslinkable monomer (E-1) are allyl methacrylate, vinyl methacrylate, 4-vinylbenzyl methacrylate, 3-vinylbenzyl methacrylate, methacryloyloxyethyl acrylate and the like. These can be used alone or in admixture thereof.

Typical examples of the crosslinkable monomer (E-2) are ethylene glycol dimethacrylate, diethylene glycol dimethacrylate, triethylene glycol dimethacrylate, tetraethylene glycol dimethacrylate, propylene glycol dimethacrylate, dipropylene glycol dimethacrylate, butane diol dimethacrylate, trimethylolpropane trimethacrylate, 2,2-bis (p-methacryloyloxyphenyl)hexafluoropropane, 2,2-bis(m-methacryloyloxyphenyl)hexafluoropropane, 2,2-bis(o-methacryloyloxyphenyl)hexafluoropropane, 2,2-bis(p-methacryloyloxyphenyl)propane, 2,2-bis(m-methacryloyloxyphenyl)propane, 2,2-bis(o-methacryloyloxyphenyl)propane, 1,4-bis(2-methacryloyloxyhexafluoroisopropyl)benzene, 1,3-bis(2-methacryloyloxyhexafluoroisopropyl)benzene, 1,2-bis(2-methacryloyloxyhexafluoroisopropyl)benzene, 1,4-bis(2-methacryloyloxyisopropyl)benzene, 1,3-bis(2-methacryloyloxyisopropyl)benzene, 1,2-bis(2-methacryloyloxyisopropyl)benzene and the like. These can be used alone or in admixture thereof.

It is important to keep a short distance between crosslinking points in order to obtain desirable mechanical properties. Furthermore, low molecular weight compounds are preferable from the viewpoint of polymerizability of the crosslinkable monomers.

The crosslinkable monomer (E) used in the present invention comprises a crosslinkable monomer (E-1) containing different polymerizable groups, i.e., at least one group selected from acryloyl group, vinyl group and allyl group, and another group of methacryloyl group, and a crosslinkable monomer (E-2) containing the same polymerizable groups, i.e., at least two methacryloyl groups. These crosslinkable monomers (E-1) and (E-2) are used together with the polysiloxane macromonomer (A) which acts as a high molecular weight crosslinkable monomer. The polysiloxane macromonomer (A) has a group selected from acryloyl group, vinyl group and allyl group, and can combine segments comprising monomers which have acryloyl group, vinyl group and allyl group with each other effectively. Herein, when ethylene glycol dimethacrylate, for example, is used as the crosslinkable monomer (E-2), segments containing methacryloyl groups are combined with each other. When allyl methacrylate, for example, is used as the crosslinkable monomer (E-1), a segment containing acryloyl group, vinyl group and allyl group is combined with the segments comprising monomers which have methacryloyl groups effectively. Furthermore, ethylene glycol dimethacrylate and allyl methacrylate are less toxic than a compound such as vinyl methacrylate, which means these monomers are very suitable for an ocular lens material.

In this way, simultaneous use of three kinds of monomers, namely, the polysiloxane macromonomer (A) which is a high molecular weight crosslinkable monomer, and allyl methacrylate and ethylene glycol dimethacrylate which are the crosslinkable monomer (E) imparts effective crosslinked structure to the polymer without generating a toxic effect. From these facts, it is particularly preferable to use allyl methacrylate as the crosslinkable monomer (E-1) and ethylene glycol dimethacrylate as the crosslinkable monomer (E-2) among the above crosslinkable monomers (E) in order to obtain a highly safe ocular lens material with excellent mechanical strength.

It is desired that the amount of the crosslinkable monomer (E) is at most 1 part by weight, preferably at least 0.8 part by weight based on 100 parts by weight (hereinafter referred to as parts) of the total amount of the polysiloxane macromonomer (A), the silicon-containing alkyl methacrylate (B), the hydrophilic monomer (C) and the monomer (D) in order to avoid preparing brittle ocular lens materials. It is desired that the amount is at least 0.05 part, preferably at least 0.1 part based on 100 parts of the total amount of the polysiloxane macromonomer (A), the silicon-containing alkyl methacrylate (B), the hydrophilic monomer (C) and the monomer (D) in order to improve mechanical strength of the ocular lens material and achieve sufficient effect to impart durability.

As mentioned above, the crosslinkable monomer (E) comprising two kinds of monomer having different polymerizable groups and the polysiloxane macromonomer (A) which is a high molecular weight crosslinkable monomer are used at the same time as crosslinkable components in the present invention. As a result, copolymerizability with the silicon-containing alkyl methacrylate (B), the hydrophilic monomer (C) and the monomer (D) is remarkably improved to enhance various properties of the ocular lens material to be obtained. It is more preferable that the ratios of polymerizable groups in each monomer are defined by, for example, the following conditions.

Defining $\alpha$ as the total number of moles of acryloyl group, vinyl group and allyl group in the hydrophilic monomer (C) and the monomer (D); $\beta$ as the total number of moles of methacryloyl group in the silicon-containing alkyl methacrylate (B) and the monomer (D); $\gamma$ as the total number of moles of acryloyl group, vinyl group and allyl group in the polysiloxane macromonomer (A) and the crosslinkable monomer (E); and $\delta$ as the total number of moles of methacrylol group in the crosslinkable monomer (E), it is preferable that these $\alpha$, $\beta$, $\gamma$ and $\delta$ satisfy both conditions of $\alpha/\gamma=20$ to 80 and $\beta/\delta=15$ to 30.

The above $\alpha/\gamma$ is desirably at least 20, preferably at least 25 from the viewpoint of avoiding the risk that crosslinking density in a polymer containing acryloyl group, vinyl group and/or allyl group is too high, causing the ocular lens material to have remarkably increased hardness or decreased elongation. The above $\alpha/\gamma$ is desirably at most 80, preferably at most 75 from the viewpoint of avoiding the risk that many monomers containing acryloyl group, vinyl group and/or allyl group remain without being crosslinked, resulting in increase of residual monomers, by which surface of the ocular lens material is made sticky or more frictional.

The above $\beta/\delta$ is at least 15, preferably at least 16 in order to avoid excessive increase of crosslinked methacryloyl group and lowering of flexibility of the ocular lens material. The above $\beta/\delta$ is at most 30, preferably at most 28 in order to avoid growth of domain containing methacryloyl group in a polymer and lowering of transparency of the ocular lens material.

In the present invention, it is further preferable that the amount of the above crosslinkable monomer (E) is at most 1 part based on 100 parts in total of the polysiloxane macromonomer (A), the silicon-containing alkylmethacrylate (B), the hydrophilic monomer (C) and the monomer (D), $\alpha/\gamma=20$ to 80 and $\beta/\delta=15$ to 30 from the viewpoint that it is possible to improve copolymerizability of the monomer mixture and various properties of the ocular lens material.

The ratio of crosslinking point which is the ratio of $(\alpha/\gamma)$ to $(\beta/\delta)$ means the ratio of probability for generation of crosslinking point of acryloyl group, vinyl group or allyl group to probability for generation of crosslinking point of methacryloyl group on condition that all of the polymerizable groups in the crosslinkable components are to be copolymerized with monomers having the identical polymerizable group. The ratio of crosslinking point $(\alpha/\gamma)/(\beta/\delta)$ is preferably near 1 from the viewpoint of uniformity of the copolymer. Actually, however, the ratio is preferably 1 to 3 considering low reactivity of allyl group in particular. When the ratio of crosslinking point is too large, there is a tendency that crosslinked structure becomes uneven, transparency of the ocular lens material is lowered and stickness or friction on the surface thereof is increased, though the ratio of monomers containing acryloyl group, vinyl group or allyl group to monomers containing methacryloyl group is also concerned. On the other hand, when the ratio of the crosslinking point is too small, methacryloyl crosslinking point is increased, resulting in a tendency that water content and flexibility of the ocular lens material is lowered while stress relaxation is increased. Accordingly, it is desired that the ratio of the crosslinking point is at least 1, preferably at least 1.1, and at most 3, preferably at most 2.9.

The ocular lens material of the present invention comprises a copolymer obtained by polymerizing a monomer mixture of the polysiloxane macromonomer (A), the silicon-containing alkyl methacrylate (B), the hydrophilic monomer (C), the monomer (D) and the crosslinkable monomer (E) as major components. It is possible to use a monomer, hereinafter referred to as another monomer (F), which has unsaturated double bond and is copolymerizable with the polysiloxane macromonomer (A), the silicon-containing alkyl methacrylate (B), the hydrophilic monomer (C), the monomer (D) and the crosslinkable monomer (E). When another monomer (F) is used, the total amount of the major components, i.e., the polysiloxane macromonomer (A), the silicon-containing alkyl methacrylate (B), the hydrophilic monomer (C), the monomer (D) and the crosslinkable monomer (E) is at least 70% by weight, preferably at least 80% by weight based on the monomer mixture from the viewpoint of excellent oxygen permeability, mechanical strength, flexibility, surface wettability and feeling of wearing, and low frictional property of the ocular lens material.

When another monomer (F) is used, it is preferable to adjust the amount of another monomer (F) so that the ratio of $\alpha$ to $\gamma$, $\alpha/\gamma$, is in the range of 20 to 80, the ratio of $\beta$ to $\delta$, $\beta/\delta$, is in the range of 15 to 30 and the ratio of crosslinking point $(\alpha/\gamma)/(\beta/\delta)$ is in the range of 1 to 3.

For the purpose of, for example, imparting hardness or softness by adjusting degree of hardness of an ocular lens material, a monomer for adjusting hardness can be used as another monomer (F).

Typical examples of the monomer for adjusting hardness are an alkoxyalkyl(meth)acrylate such as 2-ethoxyethyl (meth)acrylate, 3-ethoxypropyl(meth)acrylate, 2-methoxyethyl(meth)acrylate or 3-methoxypropyl(meth)acrylate; an alkylthioalkyl(meth)acrylate such as ethylthioethyl(meth) acrylate or methylthioethyl(meth)acrylate; styrene; $\alpha$-methylstyrene; an alkylstyrene such as a methylstyrene, an ethylstyrene, a propylstyrene, a butylstyrene, a t-butylstyrene, an isobutylstyrene or a pentylstyrene; an alkyl-$\alpha$-methylstyrene such as a methyl-$\alpha$-methylstyrene, an ethyl-$\alpha$-methylstyrene, a propyl-$\alpha$-methylstyrene, a butyl-$\alpha$-methylstyrene, a t-butyl-$\alpha$-methylstyrene, an isobutyl-$\alpha$-methylstyrene or a pentyl-$\alpha$-methylstyrene; and the like. These can be used alone or in admixture thereof.

It is desired that the amount of the monomer for adjusting hardness is at least 1% by weight, preferably at least 3% by weight in the monomer mixture to impart desirable hardness or softness to the ocular lens material sufficiently. It is desired that the amount is at most 30% weight, preferably at most 20% by weight to avoid lowering of oxygen permeability and mechanical strength of the ocular lens material.

For the purpose of, for example, improving oxygen permeability of an ocular lens material, a silicon-containing alkyl acrylate can be used as another monomer (F).

Typical examples of the silicon-containing alkyl acrylate are trimethylsiloxydimethylsilylmethyl acrylate, trimethylsiloxydimethylsilylpropyl acrylate, methylbis(trimethylsiloxy)silylpropyl acrylate, tris(trimethylsiloxy)silylpropyl acrylate, mono[methylbis(trimethylsiloxy)siloxy]bis(trimethylsiloxy)silylpropyl acrylate, tris[methylbis(trimethylsiloxy)siloxy]silylpropyl acrylate, methylbis(trimethylsiloxy)silylpropylglyceryl acrylate, tris(trimethylsiloxy)silylpropylglyceryl acrylate, mono[methylbis(trimethylsiloxy)siloxy]bis(trimethylsiloxy)silylpropylglyceryl acrylate, trimethylsilylethyltetramethyldisiloxypropylglyceryl acrylate, trimethylsilylmethyl acrylate, trimethylsilylpropyl acrylate, trimethylsilylpropylglyceryl acrylate, trimethylsiloxydimethylsilylpropylglyceryl acrylate, methylbis(trimethylsiloxy)silylethyltetramethyldisiloxymethyl acrylate, tetramethyltriisopropylcyclotetrasiloxanylpropyl acrylate, tetramethyltriisopropylcyclotetrasiloxybis(trimethylsiloxy)silylpropyl acrylate and the like. These can be used alone or in admixture thereof.

It is desired that the amount of the silicon-containing alkyl acrylate is at least 1% by weight, preferably at least 3% by weight in the monomer mixture to improve oxygen permeability of the ocular lens material sufficiently. It is desired that the amount is at most 30% weight, preferably at most 20% by weight to avoid lowering of surface wettability of the ocular lens material.

For the purpose of, for example, improving oxygen permeability and mechanical strength of an ocular lens material, a silicon-containing styrene derivative can be used as another monomer (F).

Examples of the silicon-containing styrene derivative are a compound represented by the formula (IX):

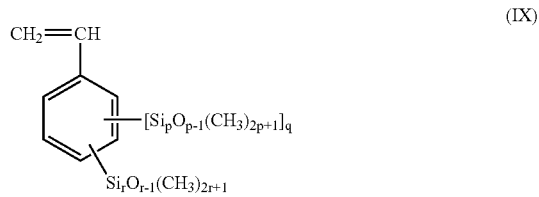

wherein p is an integer of 1 to 15, q is 0 or 1 and r is an integer of 1 to 15, and the like. When p or r is an integer at least 16, purification or synthesis of the silicon-containing styrene derivative represented by the formula (IX) is difficult, and further, hardness of the ocular lens material to be obtained tends to be lowered. When q is an integer of at least 2, synthesis of the silicon-containing styrene derivative tends to be difficult.

Typical examples of the silicon-containing styrene derivative are tris(trimethylsiloxy)silylstyrene, bis(trimethylsiloxy)methylsilylstyrene, (trimethylsiloxy)dimethylsilylstyrene, tris(trimethylsiloxy)siloxydimethylsilylstyrene, [bis(trimethylsiloxy)methylsiloxy]dimethylsilylstyrene, (trimethylsiloxy)dimethylsilylstyrene, heptamethyltrisiloxanylstyrene, nonamethyltetrasiloxanylstyrene, pentadecamethylheptasiloxanylstyrene, heneicosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris(pentamethyldisiloxy)silylstyrene, tris(trimethylsiloxy)siloxybis(trimethylsiloxy)silylstyrene, bis(heptamethyltrisiloxy)methylsilylstyrene, tris[methylbis(trimethylsiloxy)siloxy]silylstyrene, trimethylsiloxybis[tris(trimethylsiloxy)siloxy]silylstyrene, heptakis(trimethylsiloxy)trisilylstyrene, nonamethyltetrasiloxyundecyl-methylpentasiloxymethylsilylstyrene, tris[tris(trimethylsiloxy)siloxy]silylstyrene, (tristrimethylsiloxyhexamethyl)tetrasiloxy-[tris(trimethylsiloxy)siloxy]trimethylsiloxysilylstyrene, nonakis(trimethylsiloxy)tetrasilylstyrene, bis(tridecamethylhexasiloxy)methylsilylstyrene, heptamethylcyclotetrasiloxanylstyrene, heptamethylcyclotetrasiloxybis(trimethylsiloxy)silylstyrene, tripropyltetramethylcyclotetrasiloxanylstyrene, trimethylsilylstyrene and the like. These can be used alone or in admixture thereof.

It is desired that the amount of the silicon-containing styrene derivative is at least 1% by weight, preferably at least 3% by weight in the monomer mixture to improve oxygen permeability and mechanical strength of the ocular lens material sufficiently. It is desired that the amount is at most 30% weight, preferably at most 20% by weight to avoid lowering of surface wettability of the ocular lens material.

For the purpose of, for example, improving flexibility and surface wettability of an ocular lens material, a hydrophilic monomer having methacryloyl group can be used as another monomer (F).

Examples of the hydrophilic monomer having methacryloyl group are a methacrylamide monomer such as methacrylamide, N,N-dimethylmethacrylamide, N,N-diethylmethacrylamide, N,N-dimethylaminopropylmethacrylamide, N-isopropylmethacrylamide, or methacryloylmorpholine; a hydroxyalkyl metacrylate such as 2-hydroxyethyl methacrylate, hydroxypropyl methacrylate or hydroxybutyl methacrylate; an (alkyl)aminoalkyl methacrylate such as 2-dimethylaminoethyl methacrylate or 2-butylaminoethyl methacrylate; alkylene glycol monomethacrylate such as ethylene glycol monomethacrylate or propylene glycol monomethacrylate; a poly(alkylene glycol)monomethacrylate such as polyethylene glycol monomethacrylate or polypropylene glycol monomethacrylate; methacrylic acid; and the like. These can be used alone or in admixture thereof.

It is desired that the amount of the hydrophilic monomer having methacryloyl group is at least 1% by weight, preferably at least 3% by weight in the monomer mixture to improve flexibility and surface wettability of the ocular lens material sufficiently. It is desired that the amount is at most 30% by weight, preferably at most 20% by weight to avoid lowering of oxygen permeability of the ocular lens material.

For the purpose of, for example, imparting ultraviolet-ray (UV) absorbing property or giving color to a material, a polymerizable UV absorbent, a polymerizable dyestuff and a polymerizable UV absorbing dyestuff can be used as another monomer (F).

Concrete examples of the above polymerizable UV absorbent are polymerizable benzophenone derivatives such as 2-hydroxy-4-(meth)acryloyloxybenzophenone, 2-hydroxy- 4-(meth)acryloyloxy-5-t-butylbenzophenone, 2-hydroxy-4-(meth)acryloyloxy-2',4'-dichlorobenzophenone or 2-hydroxy-4-(2'-hydroxy-3'-(meth)acryloyloxypropoxy) benzophenone; polymerizable benzotriazole derivatives such as 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole, 2-(2'-hydroxy-5'-(meth)acryloyloxypropylphenyl)-2H-benzotriazole or 2-(2'-hydroxy-5'-(meth)acryloyloxypropyl-3'-t-butylphenyl)-5-chloro-2H-benzotriazole; a polymerizable salicylic acid derivatives such as phenyl 2-hydroxy-4-methacryloyloxymethylbenzoate; methyl 2-cyano-3-phenyl-3-(3'-(meth)acryloyloxyphenyl)propenate; and the like. These can be used alone or in admixture thereof.

Concrete examples of the above polymerizable dyestuff are polymerizable azo compounds such as 1-phenylazo-4-(meth)acryloyloxynaphthalene, 1-phenylazo-2-hydroxy-3-(meth)acryloyloxynaphthalene, 1-naphthylazo-2-hydroxy-3-(meth)acryloyloxynaphthalene, 1-(α-anthrylazo)-2-hydroxy-3-(meth)acryloyloxynaphthalene, 1-((4'-phenylazo)phenyl)azo)-2-hydroxy-3-(meth) acryloyloxynaphthalene, 1-(2',4'-xylylazo)-2-(meth)acryloyloxynaphthalene, 1-(o-tolylazo)-2-(meth)acryloyloxynaphthalene, 2-(m-(meth)acryloylamide-anilino)-4,6-bis(1'-(o-tolylazo)-2'-naphthylazo)-1,3,5-triazine, 2-(m-vinylanilino)-4-(4'-nitrophenylazo)-anilino)-6-chloro-1,3,5-triazine, 2-(1'-(o-tolylazo)-2'-naphthyloxy)-4-(m-vinylanilino)-6-chloro-1,3,5-triazine, 2-(p-vinylanilino)-4-(1'-(o-tolylazo)-2'-naphthylamino)-6-chloro-1,3,5-toriazine, N-(1'-(o-tolylazo)-2'-naphthyl)-3-vinylphthalic acid monoamide, N-(1'-(o-tolylazo)-2'-naphthyl)-6-vinylphthalic acid monoamide, mono(4'-(p-sulfophenylazo)-1'-naphthyl) 3-vinylphthalate, mono(4'-(p-sulfophenylazo)-1'-naphthyl) 6-vinylphthalate, 3-(meth)acryloylamide-4-phenylazophenol, 3-(meth)acryloylamide-4-(8'-hydroxy-3',6'-disulfo-1'-naphthylazo)phenol, 3-(meth)acryloylamide-4-(1'-phenylazo-2'-naphthylazo)phenol, 3-(meth)acryloylamide-4-(p-tolylazo)phenol, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(m-(4'-hydroxy-1'-phenylazo)anilino)-6-isopropenyl-1,3,5-triazine, 2-amino-4-(N-methyl-p-(4'-hydroxyphenylazo) anilino)-6-isopropenyl-1,3,5-triazine, 2-amino-4-(m-(3'-methyl-1'-phenyl-5'-hydroxy-4'-pyrrazolylazo)anilino)-6-isopropenyl-1,3,5-triazine, 2-amino-4-(N-methyl-p-(3'-methyl-1'-phenyl-5'-hydroxy-4'-pyrrazolylazo)anilino)-6-isopropenyl-1,3,5-triazine, 2-amino-4-(p-phenylazoanilino)-6-isopropenyl-1,3,5-triazine or 4-phenylazo-7-(meth)acryloylamide-1-naphthol; polymerizable anthraquinone derivatives such as 1,5-bis((meth)acryloylamino)-9,10-anthraquinone, 1-(4'-vinylbenzoylamide)-9,10-anthraquinone, 4-amino-1-(4'-vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(3'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis(4'-vinylbenzoylamide)-9,10-anthraquinone, 1,4-bis(4'-isopropenylbenzolyamide)-9,10-anthraquinone, 1,5'-bis(4'-vinylbenzoylamide)-9,10-anthraquinone, 1,5-bis(4'-isopropenylbenzoylamide)-9,10-anthraquinone, 1-methylamino-4-(3'-vinylbenzoylamide)-9,10-anthraquinone, 1-methylamino-4-(4'-vinylbenzoyloxyethylamino)-9,10-anthraquinone, 1-amino-4-(3'-vinylphenylamino)-9,10-anthraquinone-2-sulfonic acid, 1-amino-4-(4'-vinylphenylamino)-9,10-anthraquinone-2-sulfonic acid, 1-amino-4-(2'-vinylbenzylamino)-9,10-anthraquinone-2-sulfonic acid, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 1-(β-ethoxycarbonylallylamino)-9,10-anthraquinone, 1-(β-carboxyallylamino)-9,10-anthraquinone, 1,5-di-(β-carboxyallylamino)-9,10-anthraquinone, 1-(β-isopropoxycarbonylallylamino)-5-benzoylamide-9,10-anthraquinone, 2-(3'-(meth) acryloylamide-anilino)-4-(3'-(3''-sulfo-4''-aminoanthraquinone-1''-yl)-amino-anilino)-6-chloro-1,3,5-triazine, 2-(3'-(meth)acryloylamide-anilino)-4-(3'-(3''-sulfo-4''-aminoanthraquinone-1''-yl)-amino-anilino)-6-hydorazino-1,3,5-triazine, 2,4-bis-((4''-methoxyanthraquinone-1''-yl)-amino)-6-(3'-vinylanilino)-1,3,5-triazine or 2-(2'-vinylphenoxy)-4-(4'-(3''-sulfo-4''-aminoanthraquinone-1''-yl-amino)-anilino)-6-chloro-1,3,5-triazine; polymerizable nitroxide compounds such as o-nitroanilinomethyl (meth)acrylate; polymerizable phtalocyanine dyestuff such as (meth)acryloyl-modified tetramino copper phthalocyanine or (meth)acryloyl-modified (dodecanoyl-modified tetramino copper phthalocyanine); and the like. These can be used alone or in admixture thereof.

Concrete examples of the above polymerizable UV dyestuff are polymerizable benzophenon derivatives such as 2,4-dihydroxy-3-(p-styrenoazo)benzophenone, 2,4-dihydroxy-5-(p-styrenoazo)benzophenone, 2,4-dihydroxy-3-(p-(meth)acryloyloxymethylphenylazo)benzophenone, 2,4-dihydroxy-5-(p-(meth)acryloyloxymethylphenylazo) benzophenone, 2,4-dihydroxy-3-(p-(meth)acryloyloxyethylphenylazo)benzophenone, 2,4-dihydroxy-5-(p-(meth)acryloyloxyethylphenylazo)benzophenone, 2,4-dihydroxy-3-(p-(meth)acryloyloxypropylphenylazo) benzophenone, 2,4-dihydroxy-5-(p-(meth) acryloyloxypropylphenylazo)benzophenone, 2,4-dihydroxy-3-(o-(meth)acryloyloxymethylphenylazo) benzophenone, 2,4-dihydroxy-5-(o-(meth) acryloyloxymethylphenylazo)benzophenone, 2,4-dihydroxy-3-(o-(meth)acryloyloxyehtylphenylazo) benzophenone, 2,4-dihydroxy-5-(o-(meth) acryloyloxyethylphenylzao)benzophenone, 2,4-dihydroxy-3-(o-(meth)acryloyloxypropylphenylazo)benzophenone, 2,4-dihydroxy-5-(o-(meth)acryloyloxypropylphenylazo) benzophenone, 2,4-dihydroxy-3-(p-(N,N-di(meth)acryloyloxyethylamino)phenylazo)benzophenone, 2,4-dihydroxy-5-(p-(N,N-di(meth)acryloyloxyethylamino)phenylazo) benzophenone, 2,4-dihydroxy-3-(o-(N,N-di(meth) acryloyloxyethylamino)phenylazo)benzophenone, 2,4-dihydroxy-5-(o-(N,N-di(meth)acryloyloxyethylamino)phenylazo)benzophenone, 2,4-dihydroxy-3-(p-(N-ethyl-N-(meth) acryloyloxyethylamino)phenylazo)benzophenone, 2,4-dihydroxy-5-(p-(N-ethyl-N-(meth)acryloyloxyethylamino) phenylazo)benzophenone, 2,4-dihydroxy-3-(o-(N-ethyl-N-(meth)acryloyloxyethylamino)phenylazo)benzophenone, 2,4-dihydroxy-5-(o-(N-ethyl-N-(meth)acryloyloxyethylamino)phenylazo)benzophenone, 2,4-dihydroxy-3-(p-(N-ethyl-N-(meth)acryloylamino)phenylazo)benzophenone, 2,4-dihydroxy-5-(p-(N-ethyl-N-(meth)acryloylamino)phenylazo)benzophenone, 2,4-dihydroxy-3-(o-(N-ethyl-N-(meth)acryloylamino)phenylazo)benzophenone or 2,4-dihydorxy-5-(o-(N-ethyl-N-(meth)acryloylamino)phenylazo) benzophenone; polymerizable benzoic acid derivatives such as phenyl 2-hydroxy-4-(p-styrenoazo)benzoate; and the like. These can be used alone or in admixture thereof.

It is desired that the amount of the polymerizable UV absorbing monomer, the polymerizable dyestuff and the polymerizable UV absorbing dyestuff is at most 3 parts, preferably 0.01 to 2 parts based on 100 parts in total of the monomer mixture depending heavily on the thickness of the lens. When the amount is more than 3 parts, mechanical strength and the like of the ocular lens material tend to be lowered. Further, the material is not suitable for an ocular lens such as a contact lens which directly contacts with organic tissues and an intraocular lens which is inserted within a living organ in consideration of the toxic effect of the UV absorbing monomer or the dyestuff. In particular, when the amount of the dyestuffs is too large, an ocular lens becomes too deep in color and transparency of the lens is lowered, making it difficult for the lens to transmit visible-light.

To obtain a copolymer which constitutes an ocular lens material of the present invention, a monomer mixture is suitably prepared by adjusting the amounts of the polysiloxane macromonomer (A), the silicon-containing alkyl methacrylate (B), the hydrophilic monomer (C), the monomer (D) and the crosslinkable monomer (E), and if necessary, another monomer (F) and polymerized with heating and/or irradiation of ultraviolet ray by means of a molding method.

In case of polymerization with heating a monomer mixture by means of a molding method, the monomer mixture and a radical polymerization initiator are mixed and put in a mold shaped like a desired ocular lens to carry out polymerization of the monomer mixture with heating the mold gradually. The obtained molded article is mechanically processed, for example, machined or polished if necessary. The whole area of at least one face or both faces, or part of at least one face or both faces of the molded article (copolymer) may be cut. It is preferable to cut at least one face or part of at least one face of the molded article (copolymer) for an ocular lens material of the present invention from the viewpoint of versatile use of products such as special lenses (bifocal or toric lenses, for example). The cutting of at least one face of the molded article (copolymer) includes blanks-molding, namely, cutting blanks obtained by polymerization by means of a molding method to shape the blanks into a desired ocular lens form. Meanwhile, the polymerization may be carried out by means of a bulk polymerization or a solution polymerization by using a solvent and the like.

Concrete examples of the above radical polymerization initiator are azobisisobutyronitrile, azobisdimethylvaleronitrile, benzoyl peroxide, t-butyl hydroperoxide, cumene hydroperoxide and the like. These can be used alone or in admixture thereof. It is desired that the amount of the above radical polymerization initiator is about 0.001 to 2 parts, preferably about 0.01 to 1 part based on 100 parts of the monomer mixture.

It is desired that the heating temperature for the monomer mixture inside the mold is at least 50° C., preferably at least 60° C. from the viewpoint of shortening polymerization time and decreasing residual monomers. It is desired that the temperature is at most 150° C., preferably at most 140° C. from the viewpoint of preventing components of the monomer mixture from evaporating and avoiding deformation of the mold, and it is desired that the heating time for the monomer mixture inside the mold is at least 10 minutes, preferably at least 20 minutes from the viewpoint of decreasing residual monomers. It is desired that the time is at most 120 minutes, preferably at most 60 minutes from the viewpoint of avoiding deformation of the mold. Meanwhile, the monomer mixture may be heated stepwise.

When a monomer mixture is polymerized with heating, it is particularly desired that, in the monomer mixture, the weight ratio of the total of the polysiloxane macromonomer (A) and the silicon-containing alkyl methacrylate (B) to the hydrophilic monomer (C), the total weight of (A) and (B)/the weight of (C), is 30/70 to 70/30, preferably 40/60 to 65/35; the weight ratio of the polysiloxane macromonomer (A) to the silicon-containing alkyl methacrylate (B), the weight of (A)/the weight of (B), is 25/75 to 75/25, preferably 40/60 to 60/40; the weight ratio of N-vinylpyrrolidone (C-1) to the hydrophilic monomer (C-2), the weight of (C-1)/the weight of (C-2), is 50/50 to 100/0, preferably 60/40 to 85/15; and the amount of the monomer (D) in the monomer mixture is 0 to 20% by weight, preferably 0 to 10% by weight in consideration of improvement of wettability and decrease in surface stickiness of the material.

In case of polymerization with irradiating a monomer mixture with ultraviolet ray by means of a molding method, the monomer mixture and a photo polymerization initiator are mixed and put in a mold shaped like a desired ocular lens to carry out polymerization of the monomer mixture with irradiating the mold with ultraviolet ray. The obtained molded article is mechanically processed, for example, cut or polished if necessary. The whole area of at least one face or both faces, or part of at least one face or both faces of the molded article (copolymer) may be cut. It is preferable to cut at least one face or part of at least one face of the molded article (copolymer) for an ocular lens material of the present invention from the viewpoint of versatile use of products such as special lenses. The cutting of at least one face of the molded article (copolymer) includes blanks-molding, namely, machining blanks into a desired ocular lens form. Meanwhile, the polymerization may be carried out by means of a bulk polymerization or a solution polymerization by using a solvent and the like. While the polymerization is carried out with ultraviolet-ray irradiation in the present invention, electron beam irradiation instead of the ultraviolet-ray irradiation may be adopted. In this case, polymerization of a monomer mixture proceeds without any photo polymerization initiator.

Concrete examples of the above photo initiator are benzoin type photo initiators such as methyl orthobenzoylbenzoate, methyl benzoylformate, benzoin methyl ether, benzoin ethyl ether, benzoin isopropyl ether, benzoin isobutyl ether or benzoin n-butyl ether; phenone type photo initiators such as 2-hydroxy-2-methyl-1-phenylpropane-1-one, p-isopropyl-α-hydroxyisobutylphenone, p-t-butyltrichloroacetophenone, 2,2-dimethoxy-2-phenylacetophenone, α,α-dichloro-4-phenoxyacetophenone or N,N-tetraethyl-4,4-diaminobenzophenone; 1-hydroxycyclohexyl phenyl ketone; 1-phenyl-1,2-propanedione-2-(o-ethoxycarbonyl) oxime; thioxanthone photo polymerization initiators such as 2-chlorothioxanthone or 2-methylthioxanthone; dibenzosvarron; 2-ethylanthraquinone; benzophenone acrylate; benzophenone; benzil; and the like. These can be used alone or in admixture thereof. A photo sensitizer may be used together with the photo initiator. It is desired that the amount of these photo initiator and photo sensitizer is about 0.001 to 2 parts, preferably about 0.01 to 1 part based on 100 parts of the monomer mixture.

In order to improve homogeneity of the components in the monomer mixture, the polymerization may be carried out in the presence of a diluent. Since a solvent capable of dissolving components of the monomer mixture is used as the diluent, the monomer mixture to which the diluent is added is homogeneous and hard to cause phase separation at polymerization, showing the advantage that the ocular lens material to be obtained does not easily become opaque.

Concrete examples of the above diluent are an alcohol having 1 to 12 carbon atoms such as ethanol, propanol, butanol, pentanol, hexanol, octanol or decanol; a ketone having 2 to 4 carbon atoms such as acetone or methyl ethyl ketone; acetonitrile; chloroform; and the like. These can be used alone or in admixture thereof. The diluent is suitably selected according to the kind of the monomer mixture.

It is desired that the amount of the diluent is at least 0.5 part, preferably at least 1 part based on 100 parts of the monomer mixture to avoid phase separation of the mixture. On the other hand, it is desired that the amount is at most 100 parts, preferably at most 80 parts based on 100 parts of the monomer mixture to avoid preparing brittle ocular lens materials.

In case of UV irradiating a monomer mixture in a mold, the irradiance on a wavelength of 365 nm is at least 0.5 mW/cm$^2$, preferably at least 1 mW/cm$^2$ from the viewpoint of shortening polymerization time, decreasing residual monomers and lowering stickiness. On the other hand, the illuminance is at most 20 mW/cm$^2$, preferably at most 15 mW/cm$^2$ from the viewpoint of preventing decomposition of the material. The time for irradiating a monomer mixture in a mold with ultraviolet ray is at least 1 minute, preferably at least 5 minutes from the viewpoint of decreasing residual monomers and improving crosslinking density to lower stickiness. On the other hand, the time is at most 80 minutes, preferably at most 70 minutes from the viewpoint of preventing cleavage of the polymer main chain or functional group and preventing deterioration of the material.

When a monomer mixture is polymerized with ultraviolet-ray irradiation, it is particularly desired that, in the monomer mixture, the weight ratio of the total of the polysiloxane macromonomer (A) and the silicon-containing alkyl methacrylate (B) to the hydrophilic monomer (C), the total weight of (A) and (B)/the weight of (C), is 40/60 to 70/30, preferably 45/55 to 65/35; the weight ratio of the polysiloxane macromonomer (A) to the silicon-containing alkyl methacrylate (B), the weight of (A)/the weight of (B), is 35/65 to 75/25, preferably 35/65 to 60/40; the weight ratio of N-vinylpyrrolidone (C-1) to the hydrophilic monomer (C-2), the weight of (C-1)/the weight of (C-2), is 50/50 to 100/0, preferably 60/40 to 85/15; and the amount of the monomer (D) in the monomer mixture is 0 to 20% by weight, preferably 0 to 10% by weight in consideration of decreasing residual monomers, making the surface of the material less frictional and improving wettability.

In both cases of polymerization with heating the monomer mixture and with irradiating the monomer mixture with ultraviolet-ray or electron beam, a haptic may be produced separately from a lens and then attached to the lens, or a haptic may be formed with a lens in one united body for an intraocular lens.

To impart hydrophilic property and lipid-stain resistance to a surface of an ocular lens material, the surface may be treated with plasma under, for example, oxygen gas, inert gas or air. The plasma may be generated between the electrodes of a plasma generator under reduced pressure of about 1.3 to 1.3×10$^2$ Pa or normal pressure for the treatment with the plasma.

The thus-obtained ocular lens material of the present invention has various properties at one time, and preferably shows, for example, the following values for each property.

It is desired that the dynamic frictional forcebg of the ocular lens material is at most 0.025 N, preferably at most 0.023 N. The smaller the dynamic frictional force is, the less frictional the ocular lens material is.

It is desired that the contact angle of the ocular lens material at 25° C. is at most 35°, preferably at most 34°. The smaller the contact angle is, the more excellent surface wettability the ocular lens material has.

Methods for measuring the above dynamic frictional force and contact angle is described below.

Having excellent surface wettability and low surface frictional property in addition to high oxygen permeability and high mechanical strength in this way, the ocular lens material of the present invention can be suitably used for a contact lens, intraocular lens, artificial cornea and the like.

Next, the ocular lens material of the present invention is explained in detail based on Examples, but the present invention is not limited thereto.

EXAMPLES 1 TO 8 AND COMPARATIVE EXAMPLES 1 TO 8

Each ocular lens component obtained by mixing a monomer mixture and a polymerization initiator shown in Tables 1 and 2 was injected into a mold having shape of a contact lens (made of polypropylene, corresponding to a contact lens having a diameter of about 13 mm and a thickness of 0.1 mm) or a mold having shape of a film (made of polypropylene, corresponding to a film having a diameter of about 15 mm and a thickness of 0.2 mm).

Next, photo polymerization was carried out by UV irradiating the mold, the irradiance on a wavelength of 365 nm is 2 mW/cm$^2$ for 60 minutes by using a black light to give a copolymer.

The obtained copolymer was removed from the mold and equilibrated in phosphate-buffered physiological Saline Solution to obtain an ocular lens material.

EXAMPLES 9 AND 10

Each ocular lens component obtained by mixing a monomer mixture and a polymerization initiator shown in Table 1 was injected into a mold having shape of a contact lens (made of polypropylene, corresponding to a contact lens having a diameter of about 13 mm and a thickness of 0.1 mm) or a mold having shape of a film (made of polypropylene, corresponding to a film having a diameter of about 15 mm and a thickness of 0.2 mm).

Next, thermal polymerization was carried out by heating the mold in a drying oven set to 100° C. for 40 minutes to give a copolymer.

The obtained copolymer was removed from the mold and equilibrated in phosphate-buffered physiological Saline Solution to obtain an ocular lens material.

EXAMPLES 11 TO 13 AND COMPARATIVE EXAMPLE 9

Each ocular lens component obtained by mixing a monomer mixture and a polymerization initiator shown in Table 3 was injected into a mold having shape of a contact lens (made of polypropylene, corresponding to a contact lens having a diameter of about 13 mm and a thickness of 0.1 mm) or a mold having shape of a film (made of polypropylene, corresponding to a film having a diameter of about 15 mm and a thickness of 0.2 mm).

Next, photo polymerization was carried out by irradiating the mold, the irradiance on a wavelength of 365 nm is 2 mW/cm$^2$ for 60 minutes by using a black light to give a copolymer.

The obtained copolymer was removed from the mold and equilibrated in phosphate-buffered physiological Saline Solution to obtain an ocular lens material.

TEST EXAMPLE 1

Transparency and surface lubricity of the ocular lens materials obtained in Examples 1 to 13 and Comparative Examples 1 to 9 (contact lenses about 13 mm in diameter and 0.1 mm in thickness) were examined according to the following methods. The results are shown in Tables 4 to 6.

(a) Transparency

Appearance of the contact lens was visually observed and evaluated based on the following criteria.

[Evaluation Criteria]

A: The lens has no cloud, and is particularly excellent in transparency and most suitable for a contact lens.
B: The lens has little cloud but is transparent enough for a contact lens.
C: The lens has opaque, and is inferior in transparency and difficult to use the lens as a contact lens.
D: The lens has remarkable opaque, and is extremely inferior in transparency and impossible to be used as a contact lens.

(b) Surface Lubricity

A contact lens was folded into two and rubbed between fingers to examine lubricity (adhesion state of the lens with itself and adhesion state of the lens and the finger). Surface wettability was observed and evaluated based on the following criteria in addition to surface lubricity.

[Evaluation Criteria]

A: The lens is excellent in wettability and lubricity with the lens itself, and most suitable for a contact lens.
B: Creak can be slightly detected when the lens is rubbed with itself but is acceptable for use as a contact lens.
C: The lens does not adhere to fingers, but is inferior in lubricity with itself and sometimes loses the slippery movement.
D: The lens is sticky of the surface and strongly adhesive to fingers.

TEST EXAMPLE 2

Frictional property, surface wettability, flexibility, stain resistance, oxygen permeability, water content and refractive index of the ocular lens materials obtained in Examples 1 to 13 and Comparative Examples 1 to 9 (films about 15 mm in diameter and 0.2 mm in thickness) were examined according to the following methods. The results are shown in Tables 4 to 6.

(c) Frictional Property

The obtained film was fixed on the smooth surface of a cylindrical jig made of metal having a diameter of 11.28 mm and a weight of 40 g. The film was placed on a glass board moistened with distilled water so that the film contacts with the face of the glass board.

The film was then dragged at a fixed rate by using a tensile tester made by Instron Corporation to measure a dynamic frictional force (N).

The smaller the dynamic frictional force is, the more excellent surface wettability and the less frictional property the film has.

(d) Surface Wettability

Contact angle (°) of each film was measured in saline of 25° C. according to a bubble method by using a contact anglemeter G-I, 2MG made by Erma Sales Co., Ltd. Each contact angle in Tables 4 to 6 is an average value of right and left contact angles which were formed between the film and bubble when 2 μL of bubble was applied, by using a syringe, to the film which had been immersed in saline.

The smaller the contact angle is, the more excellent surface wettability the film has.

(e) Flexibility

The periphery of the obtained film was fixed and the center thereof was fixed to an apparatus for loading by using a spherical jig whose tip diameter was ⅟16 inch. Load of about 20 g was applied to the film. The loading was then stopped and stress $S_0$ (g/mm$^2$) was measured just after stopping the loading. Further, the film was allowed to stand for 30 seconds and then stress S (g/mm$^2$) was measured.

Stress relaxation coefficient (%) was calculated from these stress values $S_0$ and S on the basis of the following equation:

$$\text{Stress relaxation coefficient (\%)} = \{(S_0-S)/S_0\} \times 100$$

In case where stress relaxation coefficient is at least 15%, the film is poor in elastic recovery. Accordingly, it cannot be recognized that the film has flexibility sufficient for an ocular lens material.

(f) Stain Resistance

The obtained film was put in a glass bottle containing 2 mL of an artificial tear lipid solution, a buffer solution of pH 7, which comprises 0.3 g of oleic acid, 0.3 g of linoleic acid, 4.0 g of tripalmitic acid, 1.0 g of cetyl alcohol, 0.3 g of palmitic acid, 4.0 g of spermaceti, 0.4 g of cholesterol, 0.4 g of cholesterol palmitate and 14.0 g of yolk lecithin. The glass bottle was shaken at 37° C. for 5 hours.

After five hours, the film was picked up from the artificial tear lipid solution, and then lipid components which adhered to the film were extracted by immersing the film in 1 mL of a mixed solution of ethanol and diethyl ether (ethanol: diethyl ether=3:1 (volume ratio)). Concentrated sulfuric acid was added to 500 μL of the obtained lipid extracted solution. Thereto were further added 3 mg of vanillin and 2 mL of phosphoric acid. Then adhering lipid amount (mg/cm$^2$) of the film was quantitated.

When adhering lipid amount is more than 1 mg/cm$^2$, lipid easily adheres to the film and thus lipid-stain resistance of the film is inferior.

(g) Oxygen Permeability ($Dk_{O_2}$)

Using Seikaken-type film oxygen-gas permeator made by RIKASEIKI KOGYO CO., LTD., oxygen permeability of the film having a thickness of 0.2 mm was measured in saline of 35° C. The unit of oxygen permeability is (cm$^2$/sec)(mLO$_2$/(mL×hPa)), and each value shown in Tables 4 to 6 was obtained by multiplying the measured value by $10^{11}$.

(h) Water Content

The weight W (g) of the obtained film which had been hydrated was measured in the equilibrated swollen state. The weight $W_0$ (g) of the above hydrated film which had been dried in a dryer was also measured. Water content (% by weight) was calculated from these measured values $W_0$ and W in accordance with the following equation:

$$\text{Water content (\% by weight)} = [(W-W_0)/W] \times 100$$

(i) Refractive Index

Refractive index (no unit) of each film was measured at 25° C. under a humidity of 50% by using an Atago Refractometer 1T made by Atago Co., Ltd.

TEST EXAMPLE 3

Residual amount of monomers for each copolymer (plate) obtained in Examples 2, 4 to 6 and 12, and Comparative Examples 1, 5 and 9 was calculated according to the following method. The results are shown in Tables 4 to 6.

(j) Residual Amount of Monomers

Polymerization was carried out with irradiation of ultraviolet ray. The obtained copolymer (a plate having a weight of about 0.2 g) was removed from the mold, immersed in 10 mL of acetonitrile and kept at 50° C. for 24 hours to extract monomers.

The obtained extract was analyzed by high-performance liquid chromatography. As to N-vinylpyrrolidone and tris(trimethylsiloxy)silylpropyl methacrylate which are components of the monomer mixture, proportion of the residual monomers to the added monomers was calculated. Residual amount of the monomers (% by weight) was calculated according to the following equation:

$$\text{Residual amount of monomers (\% by weight)} = \{V \times (A-b)\}/(a \times W \times w \times 100)$$

V: amount of extractant (mL)
A: peak area of monomers
a: gradient of calibration curve
b: intercept of calibration curve
W: weight of plate (g)
w: amount of monomers in a prepolymerized mixture (% by weight)

EXAMPLES 14 AND 15

Each ocular lens component obtained by mixing a monomer mixture and a polymerization initiator shown in Table 7 was injected into a mold having shape of a button (made of polypropylene, corresponding to a button having a diameter of about 12 mm and a thickness of about 5 mm).

Next, photo polymerization was carried out by irradiating the mold with ultraviolet ray having a wavelength of 365 nm in illuminance of 2 mW/cm² for 60 minutes by using a black light to give a copolymer. The obtained copolymer was removed from the mold.

EXAMPLE 16

Each ocular lens component obtained by mixing a monomer mixture and a polymerization initiator shown in Table 7 was injected into a mold having shape of a lens (made of polypropylene, corresponding to a lens having a diameter of about 13 mm and a thickness of about 0.2 mm).

Next, thermal polymerization was carried out by heating the mold in drying oven set to 100° C. for 30 minutes to give a copolymer. The obtained copolymer was removed from the mold.

TEST EXAMPLE 4

Transparency and surface lubricity of the copolymer obtained in Examples 14 to 16 were examined according to the methods in Test Example 1. Rockwell hardness and machinability were also examined according to the following method. The results are shown in Table 8.

Rockwell hardness of the copolymer obtained in Example 16 was not measured because the test piece was thin in thickness.

(k) Rockwell Hardness (30×)

Rockwell hardness of copolymers was measured according to a Rockwell superficial hardness meter model ASD made by Akashi Corporation.

When Rockwell hardness is at least −40, machined surface is almost smooth and the obtained copolymer is suitable for an ocular lens material. When it is at least −30, cut surface has excellent smoothness and the obtained copolymer is particularly preferable for an ocular lens material.

(l) Machinability

Surface of the obtained copolymer was machined. Surface roughness was then examined by using a light microscope and evaluated based on the following criteria.

[Evaluation Criteria]
A: Surface is very smooth and cutting property is excellent.
B: Surface is almost smooth.
C: Some area of cut part is torn. Breaking or crack is observed, making the cut part whitish.
D: The obtained copolymer is too soft to be cut.

Abbreviations in Tables indicate the following compounds.
SK6006: macromonomer (A-1)
SK5001: tris(trimethylsiloxy)silylpropyl methacrylate
DMAA: N,N-dimethylacrylamide
DEAA: N,N-diethylacrylamide
2HEA: 2-hydroxyethyl acrylate
NVP: N-vinylpyrrolidone
EDMA: ethylene glycol dimethacrylate
AMA: allyl methacrylate
MMA: methyl methacrylate
Dar: 2-hydroxy-2-methyl-1-phenylpropane-1-one
ABI: 2,2'-azobis(2,4-dimethylvaleronitrile)

The amount (part) of each component of ocular lenses in Tables 1 to 3 and 7 is based on 100 parts in total of the monomer mixture excepting ethylene glycol dimethacrylate and allyl methacrylate which are the crosslinkable monomer (E).

Values of the following (1) to (6) are also shown in Tables 1 to 3 and 7.
(1) (A)+(B)/(C) (weight ratio)
(2) (A)/(B) (weight ratio)
(3) (C-1)/(C-2) (weight ratio)
(4) α/γ (molar ratio)
(5) β/δ (molar ratio)
(6) (α/γ)/(β/δ) (molar ratio)

TABLE 1

| Ex. No. | Monomer mixture | | | | | | Polymerization initiator | | Proportion of component (weight ratio) | | | Proportion of polymerizable group (molar ratio) | | (6) |
|---|---|---|---|---|---|---|---|---|---|---|---|---|---|---|
| | SK6006 | SK5001 | NVP | DMAA | EDMA | AMA | Dar | ABI | (1) (A)+(B)/(C) | (2) (A)/(B) | (3) (C-1)/(C-2) | (4) α/γ | (5) β/δ | (α/γ)/(β/δ) |
| 1 | 43.5 | 19.0 | 30.0 | 7.5 | 0.15 | 0.15 | 0.5 | — | 62.5/37.5 | 69.6/30.4 | 80/20 | 25.4 | 16.6 | 1.5 |
| 2 | 34.5 | 28.0 | 30.0 | 7.5 | 0.15 | 0.15 | 0.5 | — | 62.5/37.5 | 55.2/44.8 | 80/20 | 31.3 | 24.5 | 1.3 |
| 3 | 28.0 | 22.0 | 40.0 | 10.0 | 0.15 | 0.15 | 0.5 | — | 50/50 | 56/44 | 80/20 | 50.2 | 19.2 | 2.6 |
| 4 | 18.7 | 31.3 | 40.0 | 10.0 | 0.15 | 0.15 | 0.5 | — | 50/50 | 37.4/62.6 | 80/20 | 70.6 | 27.3 | 2.6 |
| 5 | 34.5 | 28.0 | 22.5 | 15.0 | 0.15 | 0.15 | 0.5 | — | 62.5/37.5 | 55.2/44.8 | 60/40 | 32.1 | 24.5 | 1.3 |
| 6 | 18.7 | 31.3 | 30.0 | 20.0 | 0.15 | 0.15 | 0.5 | — | 50/50 | 37.4/62.6 | 60/40 | 72.3 | 27.3 | 2.6 |
| 7 | 43.5 | 19.0 | 30.0 | 7.5 | 0.10 | 0.10 | 0.5 | — | 62.5/37.5 | 69.6/30.4 | 80/20 | 26.2 | 24.9 | 1.1 |
| 8 | 28.0 | 22.0 | 40.0 | 10.0 | 0.10 | 0.20 | 0.5 | — | 50/50 | 56/44 | 80/20 | 48.1 | 20.0 | 2.4 |
| 9 | 28.0 | 22.0 | 40.0 | 10.0 | 0.15 | 0.15 | — | 0.2 | 50/50 | 56/44 | 80/20 | 50.2 | 19.2 | 2.6 |
| 10 | 28.0 | 22.0 | 40.0 | 10.0 | 0.10 | 0.30 | — | 0.2 | 50/50 | 56/44 | 80/20 | 44.4 | 15.3 | 2.9 |

Note 1)
Effective range of (1) to (3) is as follows.
(1): 30/70~70/30
(2): 25/75~75/25
(3): 50/50~100/0
Note 2)
Preferable range of (4) to (6) is as follows.
(4): 20~80
(5): 15~30
(6): 1~3

TABLE 2

| Com. Ex. No. | Monomer mixture | | | | | | Polymerization initiator | Proportion of component (weight ratio) | | | Proportion of polymerizable group (molar ratio) | | (6) |
|---|---|---|---|---|---|---|---|---|---|---|---|---|---|
| | SK6006 | SK5001 | NVP | DMAA | EDMA | AMA | Dar | (1) (A)+(B)/(C) | (2) (A)/(B) | (3) (C-1)/(C-2) | (4) α/γ | (5) β/δ | (α/γ)/(β/δ) |
| 1 | 34.5 | 28.0 | 30.0 | 7.5 | 0.30 | — | 0.5 | 62.5/37.5 | 55.2/44.8 | 80/20 | 35.1 | 21.8 | 1.6 |
| 2 | 56.3 | 6.2 | 30.0 | 7.5 | 0.15 | 0.15 | 0.5 | 62.5/37.5 | 90/10 | 80/20 | 20.0 | 5.4 | 3.7 |
| 3 | 6.2 | 56.3 | 30.0 | 7.5 | 0.15 | 0.15 | 0.5 | 62.5/37.5 | 10/90 | 80/20 | 116.8 | 49.2 | 2.4 |
| 4 | 33.8 | 3.7 | 50.0 | 12.5 | 0.15 | 0.15 | 0.5 | 37.5/62.5 | 90/10 | 80/20 | 53.2 | 3.2 | 16.4 |
| 5 | 37.5 | 37.5 | 20.0 | 5.0 | 0.15 | 0.15 | 0.5 | 75/25 | 50/50 | 80/20 | 19.4 | 32.8 | 0.6 |
| 6 | 18.7 | 31.3 | 10.0 | 40.0 | 0.15 | 0.15 | 0.5 | 50/50 | 37.4/62.6 | 20/80 | 75.6 | 27.3 | 2.8 |
| 7 | 34.5 | 28.0 | 7.5 | 30.0 | 0.15 | 0.15 | 0.5 | 62.5/37.5 | 55.2/44.8 | 20/80 | 33.5 | 24.5 | 1.4 |
| 8 | 10.0 | 40.0 | — | 50.0 | 0.15 | 0.15 | 0.5 | 50/50 | 20/80 | 0/100 | 124.8 | 35.0 | 3.6 |

Note 1)
Effective range of (1) to (3) is as follows.
(1): 30/70~70/30
(2): 25/75~75/25
(3): 50/50~100/0
Note 2)
Preferable range of (4) to (6) is as follows.
(4): 20~80
(5): 15~30
(6): 1~3

TABLE 3

| Ex. No. | Monomer mixture | | | | | | | Polymerization initiator | Proportion of component (weight ratio) | | | Proportion of polymerizable group (molar ratio) | | (6) |
|---|---|---|---|---|---|---|---|---|---|---|---|---|---|---|
| | SK6006 | SK5001 | NVP | DEAA | 2HEA | EDMA | AMA | Dar | (1) (A)+(B)/(C) | (2) (A)/(B) | (3) (C-1)/(C-2) | (4) α/γ | (5) β/δ | (α/γ)/(β/δ) |
| 11 | 34.5 | 28.0 | 30.0 | 7.5 | — | 0.15 | 0.15 | 0.5 | 62.5/37.5 | 55.2/44.8 | 80/20 | 29.8 | 24.5 | 1.2 |

TABLE 3-continued

| | Component of ocular lens (part) | | | | | | | | Proportion of component (weight ratio) | | | Proportion of polymerizable group (molar ratio) | | |
|---|---|---|---|---|---|---|---|---|---|---|---|---|---|---|
| Ex. No. | Monomer mixture | | | | | | | Polymerization initiator | (1) | (2) | (3) (C-1)/ | (4) | (5) | (6) (α/γ)/ |
| | SK6006 | SK5001 | NVP | DEAA | 2HEA | EDMA | AMA | Dar | (A) + (B)/(C) | (A)/(B) | (C-2) | α/γ | β/δ | (β/δ) |
| 12 | 23.0 | 27.0 | 40.0 | 10.0 | — | 0.15 | 0.15 | 0.5 | 50/50 | 46/54 | 80/20 | 56.6 | 23.6 | 2.4 |
| 13 | 23.0 | 27.0 | 40.0 | — | 10.0 | 0.15 | 0.15 | 0.5 | 50/50 | 46/54 | 80/20 | 57.5 | 23.6 | 2.4 |
| Com. Ex. No. 9 | 37.5 | 37.5 | 20.0 | 5.0 | — | 0.15 | 0.15 | 0.5 | 75/25 | 50/50 | 80/20 | 18.4 | 32.8 | 0.6 |

Note 1)
Effective range of (1) to (3) is as follows.
(1): 30/70~70/30
(2): 25/75~75/25
(3): 50/50~100/0

Note 2)
Preferable range of (4) to (6) is as follows.
(4): 20~80
(5): 15~30
(6): 1~3

TABLE 4

| | | | | | | Property of ocular lens material | | | | | |
|---|---|---|---|---|---|---|---|---|---|---|---|
| Ex. No. | Trans- parency | Surface lubricity | Dynamic frictional force (N) | Contact angle (°) | Stress relaxation coefficient (%) | Stain resistance lipid (mg/cm²) | Oxygen permeability* | Water content (% by weight) | Refractive index (−) | Residual monomer (% by weight) | |
| | | | | | | | | | | NVP | SK5001 |
| 1 | A | A | 0.020 | 33 | 7 | 0.9 | 38 | 32 | 1.427 | — | — |
| 2 | A | A | 0.018 | 32 | 10 | 0.8 | 41 | 32 | 1.428 | 1.9 | 0.4 |
| 3 | A | A | 0.015 | 30 | 9 | 0.8 | 29 | 32 | 1.415 | — | — |
| 4 | A | A | 0.009 | 28 | 11 | 0.8 | 23 | 50 | 1.407 | 1.9 | 0.2 |
| 5 | A | A | 0.019 | 32 | 9 | 0.9 | 34 | 50 | 1.429 | 1.7 | 0.3 |
| 6 | A | A | 0.012 | 33 | 12 | 0.7 | 27 | 45 | 1.411 | 1.9 | 0.2 |
| 7 | A | B | 0.024 | 33 | 8 | 0.9 | 38 | 33 | 1.427 | — | — |
| 8 | A | A | 0.013 | 29 | 12 | 0.8 | 29 | 31 | 1.415 | — | — |
| 9 | A | A | 0.007 | 27 | 10 | 0.7 | 30 | 32 | 1.415 | — | — |
| 10 | A | A | 0.007 | 28 | 13 | 0.8 | 29 | 30 | 1.415 | — | — |

*(cm²/sec) (mLO₂/(mL × hPa))

TABLE 5

| | | | | | | Property of ocular lens material | | | | | |
|---|---|---|---|---|---|---|---|---|---|---|---|
| Com. Ex. No. | Trans- parency | Surface lubricity | Dynamic frictional force (N) | Contact angle (°) | Stress relaxation coefficient (%) | Stain resistance lipid (mg/cm²) | Oxygen permeability* | Water content (% by weight) | Refractive index (−) | Residual monomer (% by weight) | |
| | | | | | | | | | | NVP | SK5001 |
| 1 | A | A | 0.019 | 33 | 11 | 0.8 | 40 | 33 | 1.428 | 2.5 | 0.3 |
| 2 | A | C | 0.051 | 64 | 7 | 0.8 | 38 | 25 | 1.434 | — | — |
| 3 | A | D | 0.036 | 32 | 52 | 0.8 | 38 | 29 | 1.430 | — | — |
| 4 | D | C | 0.040 | 47 | 7 | 0.9 | 23 | 50 | 1.379 | — | — |
| 5 | A | C | 0.032 | 37 | 12 | 1.2 | 44 | 15 | 1.437 | 3.3 | 0.7 |
| 6 | A | D | 0.042 | 31 | 8 | 1.5 | 27 | 52 | 1.405 | — | — |
| 7 | A | C | 0.048 | 36 | 7 | 1.6 | 38 | 32 | 1.425 | — | — |
| 8 | A | D | 0.045 | 35 | 14 | 2.1 | 28 | 49 | 1.412 | — | — |

*(cm²/sec) (mLO₂/(mL × hPa))

TABLE 6

| | | | | | | | | | | Residual monomer (% by weight) | |
|---|---|---|---|---|---|---|---|---|---|---|---|
| Ex. No. | Trans-parency | Surface lubricity | Dynamic frictional force (N) | Contact angle (°) | Stress relaxation coefficient (%) | Stain resistance lipid (mg/cm²) | Oxygen permeability* | Water content (% by weight) | Refractive index (–) | NVP | SK5001 |
| 11 | A | A | 0.020 | 34 | 13 | 0.9 | 43 | 29 | 1.433 | — | — |
| 12 | A | A | 0.018 | 32 | 13 | 0.9 | 32 | 41 | 1.415 | 2.1 | 0.2 |
| 13 | A | A | 0.017 | — | 10 | 0.8 | 32 | 40 | — | — | — |
| Com. Ex. No. 9 | A | C | 0.015 | 39 | 15 | 1.7 | 45 | 13 | 1.438 | 3.1 | 0.5 |

*(cm²/sec) (mLO₂/(mL × hPa))

TABLE 7

| | Component of ocular lens (part) | | | | | | | | Proportion of component (weight ratio) | | | Proportion of polymerizable group (molar ratio) | | |
|---|---|---|---|---|---|---|---|---|---|---|---|---|---|---|
| | Monomer mixture | | | | | | Polymerization initiator | | (1) | (2) | (3) (C-1)/ | (4) | (5) | (6) (α/γ)/ |
| Ex. No. | SK6006 | SK5001 | NVP | DEAA | MMA | EDMA | AMA | Dar | ABI | (A) + (B)/(C) | (A)/(B) | (C-2) | α/γ | β/δ | (β/δ) |
| 14 | 22.0 | 28.0 | 40.0 | 10.0 | — | 0.15 | 0.15 | 0.5 | — | 50/50 | 44/56 | 80/20 | 61.7 | 24.5 | 2.5 |
| 15 | 22.0 | 28.0 | 38.8 | 10.0 | 1.2 | 0.15 | 0.15 | 0.5 | — | 50.6/49.4 | 44/56 | 79.5/20.5 | 60.3 | 28.9 | 2.1 |
| 16 | 22.0 | 28.0 | 38.8 | 10.0 | 1.2 | 0.15 | 0.15 | — | 0.5 | 50.6/49.4 | 44/56 | 79.5/20.5 | 60.3 | 28.9 | 2.1 |

Note 1)
Effective range of (1) to (3) is as follows.
(1): 30/70~70/30
(2): 25/75~75/25
(3): 50/50~100/0
Note 2)
Preferable range of (4) to (6) is as follows.
(4): 20~80
(5): 15~30
(6): 1~3

TABLE 8

| | Property of ocular lens material | | | |
|---|---|---|---|---|
| Ex. No. | Transparency | Surface lubricity | Rockwell hardness (–) | Machinability |
| 14 | A | A | –40 | B |
| 15 | A | A | –20 | A |
| 16 | A | A | — | A |

The results in Tables 4 to 6 prove that all of the ocular lens material of the present invention obtained in Examples 1 to 13 are excellent in transparency and surface lubricity and has high oxygen permeability, high refractive index and appropriate water content. In addition, the materials have various excellent properties including low frictional property as seen from the dynamic frictional force of at most 0.025 N, excellent flexibility as seen from the stress relaxation coefficient of at most 13%, excellent stain resistance as seen from the lipid adhering amount of less than 1 mg/cm² and excellent surface wettability as seen from contact angle of approximately 30°. Besides, the results show that the residual amount of N-vinylpyrrolidone is approximately 2% by weight and that of tris(trimethylsiloxy)silylpropyl methacrylate is approximately 0.3% by weight, indicating that the residual amount of monomers are fairly low. Accordingly, all of the ocular lens materials obtained in Examples 1 to 13 are extremely suitable for an ocular lens.

On the contrary, the results in Tables 5 to 6 show that all of the ocular lens materials obtained in Comparative Examples 1 to 9 are poor in surface lubricity and transparency, and have high frictional property, low flexibility, poor stain resistance and poor surface wettability with high residual amount of N-vinylpyrrolidone in particular. Accordingly, it was proved that these materials did not have as various excellent properties as the materials of the present invention and were inadequate for an ocular lens.

The results in Table 8 prove that all of the ocular lens material of the present invention obtained in Examples 14 to 16 have excellent transparency, surface lubricity, large Rockwell hardness and superior cutting property. Accordingly, all of the ocular lens materials of the present invention obtained in Examples 14 to 16 are extremely suitable for an ocular lens.

INDUSTRIAL APPLICABILITY

The ocular lens material of the present invention has high oxygen permeability and high mechanical strength, and in addition, excellent surface wettability and low surface frictional property.

The invention claimed is:

1. An ocular lens material comprising a copolymer prepared by polymerization with irradiating a monomer mixture with ultraviolet ray by means of a molding method, said monomer mixture containing, as main components, (A) a polysiloxane macromonomer in which a polymerizable group bonds to a siloxane main chain through at least one urethane bond, and which is represented by the formula (I):

$$A^1-U^1-(-S^1-U^2-)_n-S^2-U^3-A^2 \quad (I)$$

wherein $A^1$ is a group represented by the formula (II):

$$Y^{21}-Z^{21}-R^{31}- \quad (II)$$

in which $Y^{21}$ is acryloyl group, vinyl group or allyl group, $Z^{21}$ is oxygen atom or direct bond, and $R^{31}$ is direct bond or a linear, branched or aromatic alkylene group having 1 to 12 carbon atoms;

$A^2$ is a group represented by the formula (III):

$$-R^{34}-Z^{22}-Y^{22} \quad (III)$$

in which $Y^{22}$ is acryloyl group, vinyl group or allyl group, $Z^{22}$ is oxygen atom or direct bond, and $R^{34}$ is direct bond or a linear, branched or aromatic alkylene group having 1 to 12 carbon atoms, where $Y^{21}$ in the formula (II) and $Y^{22}$ in the formula (III) may be the same or different;

$U^1$ is a group represented by the formula (IV):

$$-X^{21}-E^{21}-X^{25}-R^{32}- \quad (IV)$$

in which each of $X^{21}$ and $X^{25}$ is independently selected from direct bond, oxygen atom and an alkylene glycol group having 1 to 6 carbon atoms, $E^{21}$ is —NHCO— group (in this case, $X^{21}$ is direct bond, $X^{25}$ is oxygen atom or an alkylene glycol group and $E^{21}$ and $X^{25}$ form urethane bond), —CONH— group (in this case, $X^{21}$ is oxygen atom or an alkylene glycol group, $X^{25}$ is direct bond and $E^{21}$ and $X^{21}$ form urethane bond) or a divalent group derived from a diisocyanate selected from a group of a saturated or unsaturated aliphatic diisocyanate, an alicyclic diisocyanate or an aromatic diisocyanate (in this case, each of $X^{21}$ and $X^{25}$ is independently selected from oxygen atom and an alkylene glycol group and $E^{21}$ and $X^{21}$, $E^{21}$ and $X^{25}$ form two urethane bonds, respectively) and $R^{32}$ is a linear or branched alkylene group having 1 to 6 carbon atoms;

each of $S^1$ and $S^2$ is independently a group represented by the formula (V):

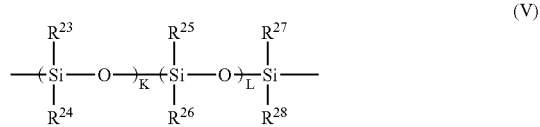

in which each of $R^{23}$, $R^{24}$, $R^{25}$, $R^{26}$, $R^{27}$ and $R^{28}$ is independently an alkyl group having 1 to 6 carbon atoms, an alkyl group having 1 to 6 carbon atoms substituted with fluorine atom or a phenyl group, K is an integer of 1 to 1,500, L is 0 or an integer of 1 to 1,499, and K+L is an integer of 1 to 1,500; $U^2$ is a group represented by the formula (VI):

$$-R^{37}-X^{27}-E^{24}-X^{28}-R^{38}- \quad (VI)$$

in which each of $R^{37}$ and $R^{38}$ is independently a linear or branched alkylene group having 1 to 6 carbon atoms, each of $X^{27}$ and $X^{28}$ is independently oxygen atom or an alkylene glycol group having 1 to 6 atoms, and $E^{24}$ is a divalent group derived from a diisocyanate selected from a group of a saturated or unsaturated aliphatic diisocyanate, an alicyclic diisocyanate or an aromatic diisocyanate (in this case, $E^{24}$ and $X^{27}$, $E^{24}$ and $X^{28}$ form two urethane bonds, respectively);

$U^3$ is a group represented by the formula (VII):

$$-R^{33}-X^{26}-E^{22}-X^{22}- \quad (VII)$$

in which $R^{33}$ is a linear or branched alkylene group having 1 to 6 carbon atoms, each of $X^{22}$ and $X^{26}$ is independently selected from direct bond, oxygen atom and an alkylene glycol group having 1 to 6 carbon atoms, $E^{22}$ is —NHCO— group (in this case, $X^{22}$ is oxygen atom or an alkylene glycol group, $X^{26}$ is direct bond and $E^{22}$ and $X^{22}$ form urethane bond), —CONH— group (in this case, $X^{22}$ is direct bond, $X^{26}$ is oxygen atom or an alkylene glycol group and $E^{22}$ and $X^{26}$ form urethane bond) or a divalent group derived from a diisocyanate selected from a group of a saturated or unsaturated aliphatic diisocyanate, an alicyclic diisocyanate or an aromatic diisocyanate (in this case, each of $X^{22}$ and $X^{26}$ is independently oxygen atom or an alkylene glycol group having 1 to 6 carbon atoms and $E^{22}$ and $X^{22}$, $E^{22}$, and $X^{26}$ form two urethane bonds, respectively); and n is 0 or an integer of 1 to 10, (B) a silicon-containing alkyl methacrylate, (C) a hydrophilic monomer comprising (C-1) N-vinylpyrrolidone and (C-2) a hydrophilic monomer excepting N-vinylpyrrolidone (C-1), containing acryloyl group, vinyl group or allyl group;

(D) at least one monomer selected from an alkyl(meth)acrylate and a fluorine-containing alkyl(meth)acrylate; and (E) a crosslinkable monomer comprising (E-1) a crosslinkable monomer containing methacrylol group, and at least one group selected from acryloyl group, vinyl group or allyl group, and (E-2) a crosslinkable monomer containing at least two methacryloyl groups, wherein the weight ratio of the total of the polysiloxane macromonomer (A) and the silicon-containing alkyl methacrylate (B) to the hydrophilic monomer (C), the total weight of (A) and (B)/the weight of (C), is 30/70 to 70/30, the weight ratio of the polysiloxane macromonomer (A) to the silicon-containing alkyl methacrylate (B), the weight of (A)/the weight of (B), is 25/75 to 75/25, the weight ratio of N-vinylpyrrolidone (C-1) to the hydrophilic monomer (G-2), the weight of (C-1)/the weight of (C-2), is 50/50 to 100/0, and the amount of the monomer (D) in the monomer mixture is 0 to 20% by weight, wherein the copolymer is prepared by polymerization with irradiating the monomer mixture with ultraviolet ray having a wavelenath of 365 nm in illuminance of 0.5 to 20 mW/cm² for 1 to 80 minutes, and in the monomer mixture, the weight ratio of the total of the polysiloxane macromonomer (A) and the silicon-containing alkyl methacrylate (B) to the hydrophilic monomer (C), the total weight of (A) and (B)/the weight of (C), being 40/60 to 70/30, the weight ratio of the polysiloxane macromonomer (A) to the silicon-containing alkyl methacrylate (B), the weight of (A)/the weight of (B), being 35/65 to 75/25, the weight ratio of N-vinylpyrrolidone (C-1) to the hydrophilic monomer (C-2), the weight of (C-1)/the weight of (C-2), being 50/50 to 100/0, and the amount of the monomer (D) in the monomer mixture being 0 to 20% by weight.

2. The ocular lens material of claim 1, wherein at least one face or a part of at least one face of the copolymer is cut.

3. The ocular lens material of claim 1, wherein the copolymer is prepared by polymerization with heating of the monomer mixture at 50° to 150° C. for 10 to 120 minutes, and in the monomer mixture, the weight ratio of the total of the polysiloxane macromonomer (A) and the silicon-containing alkyl methacrylate (B) to the hydrophilic monomer (C), the total weight of (A) and (B)/the weight of (C), being 30/70 to 70/30, the weight ratio of the polysiloxane macromonomer (A) to the silicon-containing alkyl methacrylate (B), the weight of (A)/the weight of (B), being 25/75 to 75/25, the weight ratio of N-vinylpyrrolidone (C-1) to the hydrophilic monomer (C-2), the weight of (C-1)/the weight of (C-2), being 50/50 to 100/0, and the amount of the monomer (D) in the monomer mixture being 0 to 20% by weight.

4. The ocular lens material of claim 1, wherein the amount of the crosslinkable monomer (E) is at least 1 part by weight based on 100 parts by weight in total of the polysiloxane macromonomer (A), the silicon-containing alkyl methacrylate (B), the hydrophilic monomer (C) and the monomer (D), and the total number of moles of acryloyl group, vinyl group and allyl group in the hydrophilic monomer (C) and the monomer (D) which is represented by $\alpha$ below;

the total number of moles of methacryloyl group in the silicon-containing alkyl methacrylate (B) and the monomer (D) which is represented by $\beta$ below;

the total number of moles of acryloyl group, vinyl group and allyl group in the polysiloxane macromonomer (A) and the crosslinkable monomer (E) which is represented by $\gamma$ below; and the total number of moles of methacrylol group in the crosslinkable monomer (E) which is represented by $\delta$ satisfy both conditions of $\alpha/\gamma=20$ to 80 and $\beta/\delta=15$ to 30.

5. The ocular lens material of claim 4, wherein the ratio of $\alpha/\gamma$ to $\beta/\delta$, $(\alpha/\gamma)/(\beta/\delta)$, is 1 to 3.

6. The ocular lens material of claim 1, wherein the crosslinkable monomer (E-1) is allyl methacrylate and the crosslinkable monomer (E-2) is ethylene glycol dimethacrylate.

7. The ocular lens material of claim 1, wherein the hydrophilic monomer (C-2) is at least one selected from acrylamide, N,N-dimethylacrylamide, N,N-diethylacrylamide, N-isopropylacrylamide, acryloylmorpholine, 2-hydroxyethyl acrylate, 2-dimethylaminoethyl acrylate and vinyl acetate.

8. The ocular lens material of claim 1, wherein the hydrophilic monomer (C-2) is N,N-dimethylacrylamide.

* * * * *